(12) United States Patent
Li et al.

(10) Patent No.: US 7,576,165 B2
(45) Date of Patent: *Aug. 18, 2009

(54) HETEROCYCLE GRAFTED MONOMERS AND RELATED POLYMERS AND HYBRID INORGANIC-ORGANIC POLYMER MEMBRANES

(75) Inventors: Siwen Li, Atlanta, GA (US); Zhen Zhou, Atlanta, GA (US); Meilin Liu, Alpharetta, GA (US); Wen Li, Ann Arbor, MI (US); Kohai Hase, Nagoya (JP)

(73) Assignees: Georgia Institute of Technology, Atlanta, GA (US); Toyota Motor Engineering & Manufacturing North America, Inc., Erlanger, KY (US)

( * ) Notice: Subject to any disclaimer, the term of this patent is extended or adjusted under 35 U.S.C. 154(b) by 221 days.

This patent is subject to a terminal disclaimer.

(21) Appl. No.: 11/044,527

(22) Filed: Jan. 26, 2005

(65) Prior Publication Data

US 2006/0111530 A1 May 25, 2006

Related U.S. Application Data

(60) Provisional application No. 60/539,641, filed on Jan. 27, 2004, provisional application No. 60/614,814, filed on Sep. 30, 2004.

(51) Int. Cl.
*C08F 26/06* (2006.01)
*C08F 24/00* (2006.01)
(52) U.S. Cl. ..................... 526/258; 526/266
(58) Field of Classification Search ............ 526/258, 526/266
See application file for complete search history.

(56) References Cited

U.S. PATENT DOCUMENTS

| | | | |
|---|---|---|---|
| 3,122,581 A | 2/1964 | Pike | 260/448.8 |
| 3,408,420 A | 10/1968 | Wiggill | 260/827 |
| 4,707,517 A | 11/1987 | Bullen et al. | 525/72 |
| 4,766,052 A | 8/1988 | Nakamura | |
| 4,923,950 A | 5/1990 | Ravaine et al. | 528/38 |
| 5,283,310 A | 2/1994 | Armand et al. | 528/30 |
| 5,389,726 A | 2/1995 | Sojka | 525/100 |
| 5,453,467 A | 9/1995 | Bamford et al. | 525/287 |
| 5,627,296 A | 5/1997 | Dauth et al. | 556/405 |
| 5,656,386 A | 8/1997 | Scherer et al. | 429/33 |
| 5,840,800 A | 11/1998 | Joffre et al. | 524/806 |
| 5,998,559 A | 12/1999 | Narang et al. | 528/14 |
| 6,096,899 A | 8/2000 | Rasmussen | |
| 6,124,060 A | 9/2000 | Akita et al. | 429/307 |
| 6,201,064 B1 | 3/2001 | Aoyama et al. | 525/63 |
| 6,264,857 B1 * | 7/2001 | Kreuer et al. | 252/500 |
| 6,310,110 B1 | 10/2001 | Markowitz et al. | 521/99 |
| 6,376,129 B2 | 4/2002 | Faure et al. | 429/306 |
| 6,423,784 B1 | 7/2002 | Hamrock et al. | 525/326.2 |
| 6,488,343 B1 | 12/2002 | Eberling et al. | 303/15 |
| 6,531,539 B2 | 3/2003 | Krafczyk et al. | 524/588 |
| 6,680,138 B1 | 1/2004 | Honma et al. | 429/33 |
| 6,713,643 B2 | 3/2004 | Pinnavaia et al. | 556/450 |
| 6,716,908 B2 | 4/2004 | Lomas et al. | 524/588 |
| 6,716,920 B2 | 4/2004 | Arhart et al. | 525/102 |
| 6,750,352 B2 | 6/2004 | Ono et al. | 548/341.5 |
| 6,756,436 B2 | 6/2004 | Rajagopalan et al. | 524/322 |
| 7,183,370 B2 * | 2/2007 | Li et al. | 528/30 |
| 2002/0127474 A1 | 9/2002 | Fleischer et al. | 429/309 |
| 2003/0144450 A1 | 7/2003 | Jacob et al. | 528/10 |
| 2004/0013925 A1 | 1/2004 | Komiya | 429/33 |
| 2004/0138490 A1 | 7/2004 | Wolter | 556/405 |
| 2005/0113547 A1 | 5/2005 | Li et al. | 528/30 |
| 2005/0135045 A1 * | 6/2005 | Nobuta et al. | 361/502 |

FOREIGN PATENT DOCUMENTS

| | | | |
|---|---|---|---|
| WO | WO 01/83092 A1 | | 8/2001 |
| WO | WO 01/84657 A2 * | | 11/2001 |
| WO | WO 03/067691 A2 | | 8/2003 |
| WO | WO 2004/005380 A1 | | 1/2004 |
| WO | WO 2004/107477 A2 | | 12/2004 |
| WO | WO 2005/001037 A2 | | 1/2005 |

OTHER PUBLICATIONS

International Search Report, PCT/US05/02922, Dec. 12, 2005.
M. Rikukawa, K. Sanui, "Proton-conducting polymer electrolyte membranes based on hydrocarbon polymers," Prog. Polym. Sci. 25 (2000) 1463-1502, Department of Chemistry, Sophia University, 7-1 Kioi-cho, Chiyoda-ku, Tokyo 102, Japan.
Michael Popall and Xin-Min Du, "Inorganic-Organic Copolymers as Solid State Ionic Conductors with Grafted Anions," Electrochimica Acta, vol. 40, No. 13-14, pp. 2305-2308, 1995.

* cited by examiner

*Primary Examiner*—William K Cheung
(74) *Attorney, Agent, or Firm*—Gifford, Krass, Sprinkle, Anderson & Citkowski, P.C.

(57) ABSTRACT

Polymers, polymer precursors, and other materials are described, having at least one heterocycle and being useful for fabrication of proton-exchange membranes (PEMs). In representative examples, the heterocycle is a fluorinated imidazole ring. The heterocycle can be chosen to have a low value of pKa, and may be a triazole ring, other nitrogen-containing heterocycle, or derivative thereof. Polymers and composites were prepared having excellent proton conductivity. Applications of these materials include fuel cells and other ion-conducting applications.

5 Claims, 4 Drawing Sheets

HETEROCYCLE GRAFTED MONOMERS AND RELATED POLYMERS AND HYBRID INORGANIC-ORGANIC POLYMER MEMBRANES

REFERENCE TO RELATED APPLICATIONS

This application claims priority from U.S. Provisional Application Ser. Nos. 60/539,641, filed Jan. 27, 2004, and 60/614,814, filed Sep. 30, 2004.

FIELD OF THE INVENTION

The present invention relates to heterocycle containing compounds, including polymers.

BACKGROUND OF THE INVENTION

Proton electrolyte membranes (PEMs) are components of fuel cells, hydrogen separation/purification, reforming/partial oxidation of hydrocarbon fuels, contaminant removal, gas sensing, and other processes relevant to energy storage and conversion. While various electrolyte membranes have been studied in many years, the existing membranes are still inadequate in performance for many applications.

The widely used perfluorosulfonic polymers (mainly Nafion®) have serious disadvantages, such as low proton conductivity over 100° C. due to loss of water, large amount of fuel crossover, dimensional changes with water contents, high cost, and the reduction of —$SO_3H$ groups under fuel cell working conditions.

These limitations have stimulated the development of many other proton conducting membranes, including polymer electrolytes with nanometer-sized hygroscopic metal oxides, sulfonated aromatic polymer membranes, polymer-$H_3PO_4$ membranes, and hybrid inorganic-organic copolymer membranes doped with proton-conductive components, including $H_3PO_4$, heteropolyacids, and —$SO_3H$ groups.

Among all above proton conducting membranes developed in recent years, polybenzimidazole (PBI)—$H_3PO_4$ membranes have the best performance. PBI—$H_3PO_4$ membranes have high proton conductivity above 150° C., good mechanical properties and high thermal stability (J. Electrochem. Soc. 1995, Vol. 142, p. L121). However, in PBI—$H_3PO_4$ membranes, $H_3PO_4$ can leach out easily from such pure organic polymer membranes, especially when $H_3PO_4$ content is high.

Meanwhile, when the content of $H_3PO_4$ is too high, the mechanical properties are degraded. Polyvinazene-$H_3PO_4$ was reported to have high proton conductivity from 150° C. to 200° C., but the decomposition of —CN groups under acidic conditions limits its application as the electrolyte material in fuel cells (Abstract of ECS meeting, Orlando, Fla., USA, October, 2003).

More recently, a polystyrene with imidazole terminated flexible side chains was synthesized. It was thermally stable up to 400° C., but the proton conductivity is too low to be used in PEM fuel cells ($\sim 10^{-4}$ S/cm at 200° C., Electrochimica Acta, 48, 2165, 2003).

Accordingly, the development of novel electrolyte membranes with high proton conductivity in low humidity, dense structure, and good mechanical properties is still the key to the successful development of high temperature PEM fuel cells and other electrochemical devices.

SUMMARY OF THE INVENTION

Compounds, including polymers and polymer precursors, are described, having at least one heterocycle and being useful for fabrication of proton-exchange membranes (PEMs). In representative examples, the heterocycle is a fluorinated imidazole ring. In other representative examples, the heterocycle is chosen to have a low value of pKa, and may be a triazole ring, other nitrogen-containing heterocycle, or derivative thereof. Good proton conductivity was observed, and PEMs fabricated with such materials can be used in fuel cells and other ion-conducting applications.

DETAILED DESCRIPTION OF THE INVENTION

Figure 1:
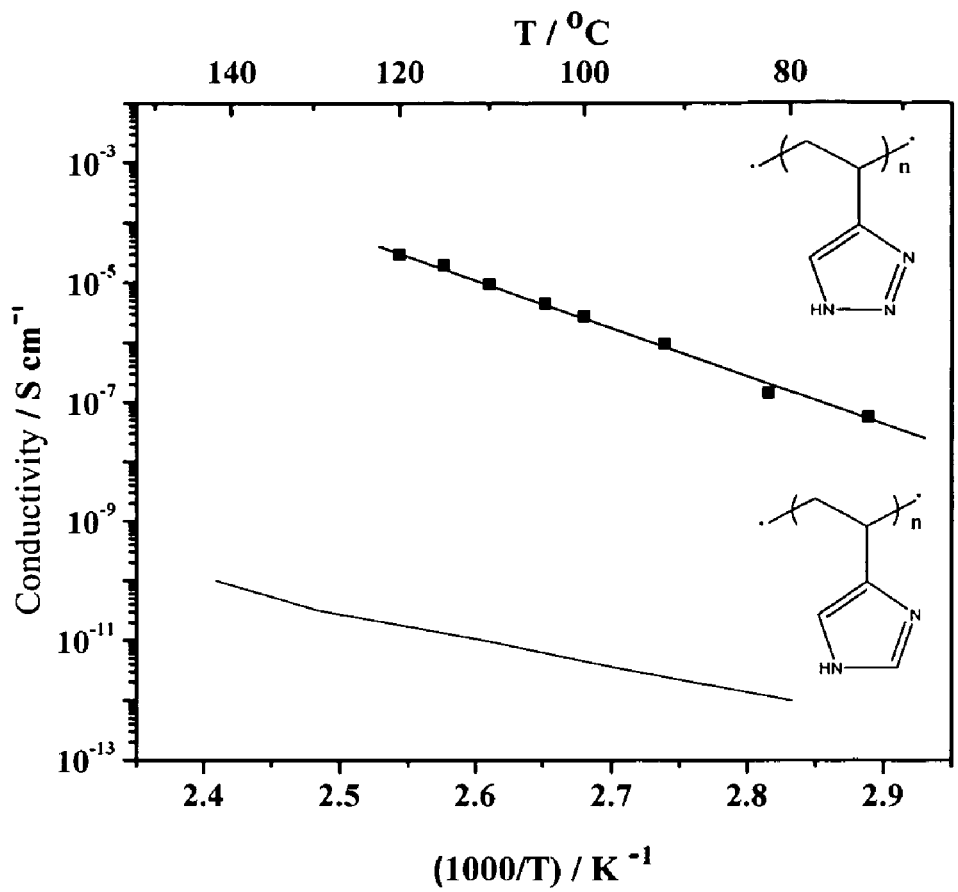
FIG. 1 shows the proton conductivity of poly(4-vinyl-1H-1,2,3-triazole) in dry air from room temperature to 120° C., compared with poly(4-vinyl-1H-imidazole)

Polymers, including hybrid inorganic-organic copolymers, and polymer precursors are described, which can be used in proton-exchange membranes (PEMs) having improved proton conductivity.

In this specification, the term 'polymer' is used to refer generally to polymers and co-polymers. The term 'polymer' can also refer to hybrid inorganic-organic polymers, such as an organically modified silica. The term 'grafted', as in heterocycle-grafted polymer, refers to groups attached to a polymer backbone, and is not limited to materials obtained by any specific synthetic method. A polymer precursor can be polymerized, or copolymerized with other precursors.

The abbreviation PEM refers to proton-exchange membranes, also known as polymer electrolyte membranes. These membranes are commonly used as proton-conducting materials in fuel cells. Polymers and other compounds according to the present invention can be used in improved PEMs. A PEM may also include other materials chosen to improve mechanical, electrical, or other properties.

Hence, a compound according to the present invention has a general structure X—Y—Z, where X includes a heterocycle, Y is a linking group, and Z is a polymerizable group, other functional group, or a polymer backbone. The linking group Y may include an alkyl chain having two or more carbon atoms. The group Z can be a polymerizable group, such as a vinyl group, epoxy group, or hydrolyzable silicon-containing group. Alternatively, Z may comprise a polymer, such as an organic polymer backbone, or polymer network such as a hybrid inorganic-organic matrix.

The heterocycle-including group X may include a nitrogen-containing heterocycle, such as imidazole, pyrazole, pyrazine, pyridine, 1,2,4-triazole, 1,2,3-triazole, pyrimidine, or derivative thereof. The group X may further include one or more electron-withdrawing groups attached to a heterocycle. Electron-withdrawing groups are well known in the chemical arts, and not all such groups are mentioned here. Examples of electron-withdrawing groups include a fluorine atom, a fluorine-containing group (such as fluoroalkyl groups, such as trifluoromethyl, other perfluoroalkyl groups, other groups including —$CF_2$—, —CHF—, —$CHF_2$, —$CH_2F$, and the like), other halogen atom (such as chlorine), other halogenated group (such as —$CClF_2$), or other electron-withdrawing group such as —$SO_2$, —$NO_2$, and —CN. Hence, in examples of the present invention, a heterocycle can be a nitrogen-containing heterocycle having one or more electron-withdrawing groups as a substituent group.

The group X can include a heterocycle having at least one atom providing a lone pair of electrons, such as N, O, or S. Heterocycles may include one or more nitrogen atoms, or some combination of N, O, and/or S. The X group may include one or more ring structures, which may or may not be fused, and one or more substituents on the ring structure(s).

The group X may be a heterocycle having a pKa of less than 7, such as less than approximately 5, for example less than approximately 3. Here, pKa=–log(Ka), and Ka is defined as the equilibrium constant of the self-dissociation of a protonated heterocycle, and all pKa values cited in this invention were measured in water at 25° C. For example, X may include a fluorinated imidazole ring having a pKa of less than approximately 3, such as 2-fluoro-1-H-imidazole. In other examples of the present invention, a heterocycle may be an example of the X group discussed above.

Hence, an improved PEM (polymer electrolyte membrane) comprises a polymer having a nitrogen-containing heterocycle attached to a polymer through a linking group, the nitrogen-containing heterocycle having a pKa of less than approximately 3, such as less than 2.6.

Another example of an improved PEM according to the present invention is a proton-conducting composite comprising an acid-group containing polymer and a compound having a first heterocycle flexibly interconnected to a second heterocycle by a linking group. The heterocycles may be the same or different, and at least one heterocycle may be a nitrogen-containing heterocycle. For example, the compound may have at least two nitrogen-containing heterocycles interconnected by one or more organic groups, such as alkyl groups or other flexible chain. The acid-group containing polymer can be a sulfonated polymer, such as Nafion™. For example, the linking group may be a chain formed by between 5 and 20 atoms, such as an alkyl chain.

In example compounds according to the present invention, imidazole rings were fluorinated to synthesize new polymers (including hybrid inorganic-organic copolymers) with fluorinated-imidazole-terminated side chains. The fluorination of imidazole rings increases the activity of the protons on imidazole rings. For example, the pKa value of imidazole is 6.99, but that of 2-fluoro-1-H-imidazole is 2.44. Proton electrolyte membranes (PEM) based on these polymers (including copolymers) and acid groups (in free form or attached on the polymer backbones) exhibit high proton conductivity, excellent mechanical properties, and high thermal stability.

Further, heterocycles and substituted heterocycles are described which provide low pKa values, and which can act as solvents for protons or proton donors (such as water and/or phosphoric acid) or other proton conducting groups in improved polymer membranes.

In examples of the present invention, new polymers, such as hybrid inorganic-organic copolymers, or composites, include heterocycle groups with suitable pKa values. Example heterocycles include one or more nitrogen atoms, and are associated with a low pKa value. The ring structure may be an aromatic ring.

Example heterocycles include, but are not limited to, 1H-1,2,4-triazole (pKa=2.4), 1H-1,2,3-triazole (pKa=1.2), 1H-benzotriazole (pKa=1.2), 2-F-1H-imidazole (pKa=2.44), 2,4,5-trifluoro-1H-imidazole (pKa=3.71), 4-trifluoromethyl-1H-imidazole (pKa=2.26), purine (pKa=2.52), pyrazole (pKa=2.61), pyrimidine (pKa=1.30), pyrazine (pKa=0.60), halogenated pyridine (pKa=+0.49 for Cl—, and –0.44 for F—).

For example, 1H-1,2,3-triazole (or the isomer 2H-1,2,3-triazole) and its organic derivatives as illustrated in Scheme 1, have a lower pKa value than imidazole, and are more stable under oxidation conditions than imidazole, so they can act as effective proton conducting groups in the materials. Derivatives of a nitrogen-containing heterocycle include heterocycles with one or more organic substituents, such as discussed in the examples below.

An imidazole ring can be readily oxidized under typical fuel cell operating conditions. Also, imidazole and the oxidized product tend to absorb on a Pt electrode to block the active sites for electrochemical reactions, often leading poisoning of the Pt electrode. Hence, an electrochemically functional fuel cell using imidazole-containing membranes is difficult to fabricate.

Fluorine groups on the imidazole ring have a strong electron-withdrawing effect, to lower the electron density of N atoms in the imidazole ring. As a result, the fluorinated imidazole has much more active N—H groups for proton conduction. Also, the binding energy of fluorinated imidazole to Pt is much lower than that of imidazole. Because of the lower electron density of fluorinated imidazole, its electrochemical stability is expected to be higher than that of imidazole. These can also be present for other halogenated heterocycles.

Hence, an example improved polymer or polymer precursor includes a heterocycle, such as a nitrogen-containing heterocycle, having a pKa of less than approximately 3, for example equal or less than approximately 2.6 (e.g. pyrazole).

(Scheme 1)

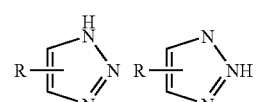

Scheme 1-1    Scheme 1-2.

Scheme 1 (1-1 and 1-2) above show possible structures for example heterocycle-containing compounds which may be incorporated into a polymer or copolymer according to the present invention. Scheme 1-1 represents 1H-1,2,3, triazole and derivatives thereof, and Scheme 1-2 represents 2H-1,2,3-triazole and derivatives thereof. R group(s) can be on C4 and/or C5 of the ring. The R group may include groups such as (but not limited to) hydrogen, halogen, alkyl, alkenyl, aromatic group, alkoxyl, ester, sulfone, ketone, thio, thiol, amino, silyl, or other flexible chain and/or functional groups (such as polymerizable groups). R may be a linking group attached to a polymer backbone.

A molecular structure such as shown in Scheme 1 can be grafted onto a polymer. For example, a precursor may have a structure represented by Scheme 1, and included in a polymer network by polymerization or co-polymerization. An R group may include a functional group which may be polymerized, co-polymerized, or allow addition to an existing polymer network.

Two or more substituent groups may be present, which may be the same or different. For example, one substituent may be a halogen, the other substituent can be a linking group, and for example, one substituent may be a halogen-containing alkyl group, the other two may be linking groups which include functional groups for polymerization. R may be a linking group, such as an organic chain, such as a hydrocarbon chain, linking the heterocycle to a polymer chain, or to a hybrid organic-inorganic matrix. R may also link the heterocycle to one or more other heterocycles (which can be the same or different). R may be, or include, substituents chosen to modify pKa of the heterocycle. Other examples will be clear from this specification.

Polymer electrolyte membranes (PEM) based on polymers or copolymers including these heterocycles (as free molecules, as immobilized molecules, or being grafted on the polymer or copolymer backbones through an organic chain), exhibit high proton conductivity, excellent mechanical properties, and high thermal stability.

Heterocycles (such as those with low pKa values) can be substantially immobilized (for example within a PEM) by linking two or more heterocycle rings together through a soft (flexible) organic chain, as shown in Schemes 2-1 and 2-2. The immobilized heterocycles can be dispersed in a sulfonated or phosphonated polymer or copolymer matrix. In addition, they can be mixed with inorganic or organic acids to obtain highly proton conducting materials.

$$R—(Htc)_n \qquad \text{(Scheme 2-1)}$$

In Scheme 2-1 above, Htc is a heterocycle; $n \geq 1$; and R is an organic chain, for example a chain including $CH_2$, $—C_6H_4$, $CF_2$, $CHF$, $O$, and/or $S$, and the like, as groups or elements).

$$(Htc)—R—(Htc) \qquad \text{(Scheme 2-2)}$$

Scheme 2-2 above illustrates another representative example, in which a pair of heterocycles Htc (which may be the same or different) are linked by a chain R. In other examples, three or more heterocycles may be linked in a linear (e.g. Htc—R—Htc—R—Htc; each Htc, R can be the same or different), star, ring, or other topography.

Scheme 3 below (3-1-3-4) illustrate general structures of heterocycle grafted polymers and copolymers according to the present invention. Here, Htc represents a heterocycle; $R_1$ and $R_4$ may be linear organic chains with $C_1$ to $C_{20}$; $R_2$ and $R_3$ may be organic compound units; $A_1$ can be an acidic group; and m and n are the numbers of the units in the polymer or copolymer. R groups may be the same or different.

(Scheme 3-1)

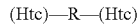

(Scheme 3-2)

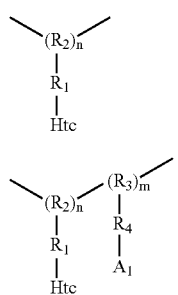

(Scheme 3-3)

(Scheme 3-4)

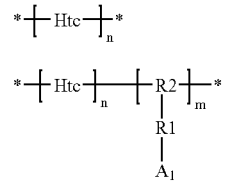

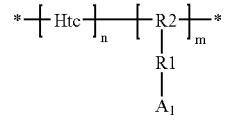

Polymers (including copolymers) with grafted heterocycles include polymers having the general structures shown in Scheme 3 (3-1 to 3-4). The main chain of an example polymer may include (but is not limited to) polyalkene ($R_2$, $R_3$=—$CRCR'R''$—), polyepoxy ($R_2$, $R_3$=—$CRCR'R''O$—), perfluoroalkene polymers ($R_2$, $R_3$=—$CF$—$CF_2$—), polysiloxane, poly-p-phenylene, polyphenylene oxide, poly-p-phenylene sulfone, polyetheretherketone, Udel polysulfone, or polybenzimidazole.

In a structure such as Scheme 3-3, a polymer backbone includes at least one heterocycle, and may comprise a repeated unit including one or more heterocycles.

To enhance the proton conductivity of membranes in low humidity environments, two kinds of composite materials can be made:

(a) polymers according to the present invention, for example as shown in Scheme 3, can have added (for example, by absorption) acids, including, but not limited to, $H_3PO_4$, $H_2SO_4$, $CF_3SO_2NHSO_2CF_3$, $CF_3SO_3H$, $CH_3SO_3H$, $CF_3PO_3H_2$, and/or other acids;

(b) polymers according to the present invention, for example as shown in Scheme 3, can be mixed with sulfonated, phosphonated, or other acid-group containing proton conducting polymers or copolymers. Sulfonated polymers or copolymers include, but are not limited to, poly(styrene sulfonic acid), sulfonated polyetheretherketone (S-PEEK), perfluorosulfonic acid, and sulfonated polyphenylene sulfide (S-PPS).

Composites may be formed comprising any polymer according to the present invention.

Scheme 4 (4-1 through 4-4) below illustrates general structures of example hybrid inorganic-organic copolymer networks according to the present invention. Here, Htc is a heterocycle; $R_1$ can be a linear organic chain with $C_1$ to $C_{20}$; $R_2$, $R_4$ and $R_6$ can be an organic group with $C_1$ to $C_{20}$; $R_3$ and $R_5$ can be an organic compound with saturated linear or branched chain; and A can be an acidic group.

(Scheme 4-1)

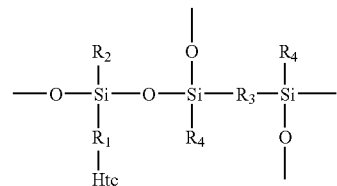

(Scheme 4-2)

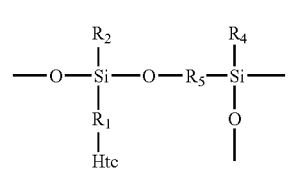

(Scheme 4-3)

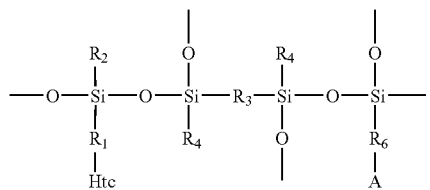

(Scheme 4-4)

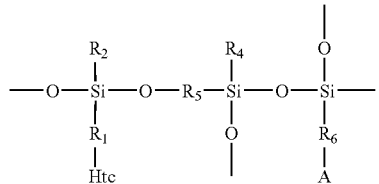

Example compounds can include one or more species of heterocycle ring grafted onto hybrid inorganic-organic polymer backbones. Several possible structure types of the hybrid inorganic-organic copolymers are represented by Scheme 4. Acid groups, such as inorganic acid groups, may also be attached to a polymer backbone.

Hybrid inorganic-organic copolymers with heterocycle-terminated organic side chains were synthesized by hydrolysis of corresponding heterocycle-grafted alkoxysilanes in certain solvents, such as methanol, ethanol, and THF, together with other alkoxysilanes and precursors as organic chain formers by water with hydrochloric acid as catalyst. The membrane manufacture process has been described in our former invention disclosures or patent applications, incorporated herein by reference, for example U.S. Prov. Pat. App. Ser. No. 60/439,985, filed Jan. 14, 2003.

In other compounds according to the present invention, imidazole rings were fluorinated to provide new polymers or hybrid inorganic-organic copolymers with fluorinated-imidazole-terminated side chains. Halogenation of imidazole rings can increase the activity of the protons on imidazole rings, increasing proton conductivity. Proton electrolyte membranes (PEM) fabricated using polymers according to the present invention incorporating fluorinated imidazole rings and inorganic acid groups (as free acid molecules, or acid groups attached to a polymer backbones) exhibit high proton conductivity, excellent mechanical properties, and high thermal stability.

Scheme 5 (5-1 and 5-2) illustrates examples of such fluorinated-imidazole ring grafted polymers. The main chain of the polymer may include groups such as, but not limited to, polyalkene ($R_2$, $R_3$=—CRCR'R"—), polyepoxy ($R_2$, $R_3$=—CRCR'R"—), perfluoroalkene polymers ($R_2$, $R_3$=—CF—CF_2$—), and the like.

In Scheme 5, $A_1$ and $A_2$ can be —H, —F, —$CF_3$, or —$C_2F_5$ groups, where at least one of $A_1$ and $A_2$ is F or a fluorine containing group); $R_1$ and $R_4$ can be linear organic chains with C1 to C20 (1-20 carbon atoms); $R_2$ and $R_3$ are organic compound units; $A_3$ is an acidic group; and m and n are the numbers of the units in the polymer or copolymers.

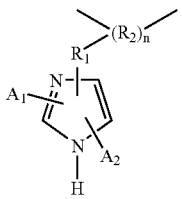

Scheme 5-1

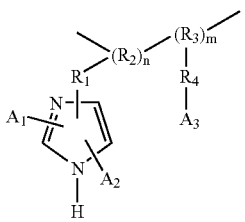

Scheme 5-2

To enhance the proton conductivity of membranes formed using the polymers of Scheme 5 in low humidity environments, the polymers can absorb acids, including, but not limited to, $H_3PO_4$, $HSO_4$, $CF_3SO_2NHSO_2CF_3$, $CF_3SO_3H$, $CH_3SO_3H$, $CF_3PO_3H_2$, and others. Acids can be attached to the polymer backbone, or included as free acid molecules, absorbed into a polymer membrane, or a composite formed with an acid-group containing polymer or other compound.

Scheme 6 (6-1 through 6-4) below shows example hybrid inorganic-organic copolymers. Here, $A_1$ and $A_2$ can be —H, —F, —$CF_3$, —$C_2F_5$ group, or similar, where at least one of $A_1$ and $A_2$ is —F or a fluorine-containing group; $R_1$ can be a linear organic chain with C1 to C20 (1-20 carbon atoms); $R_2$, $R_4$ and $R_6$ are organic groups with $C_1$ to $C_{20}$; $R_3$ and $R_5$ are organic groups with saturated linear or branched chains; and $A_3$ is an acidic group. Organic groups may be the same or different.

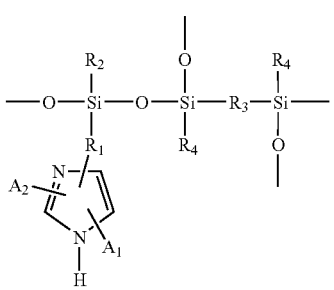

Scheme 6-1

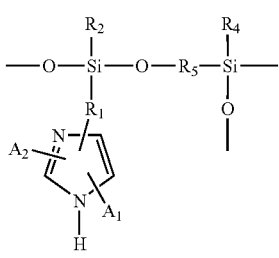

Scheme 6-2

Scheme 6-3

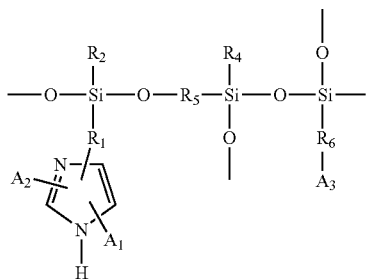

Scheme 6-4

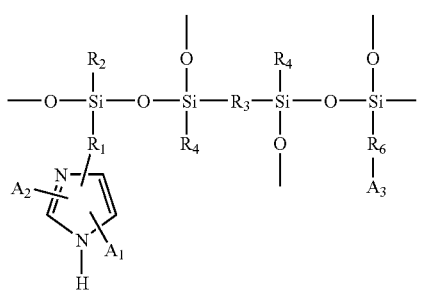

Scheme 6 (6-1 to 6-4) shows several possible general structure types for hybrid inorganic-organic copolymers according to the present invention. The hybrid inorganic-organic copolymers with fluorinated-imidazole-ring-terminated organic side chains were synthesized by hydrolysis of corresponding fluorinated-imidazole-grafted alkoxysilanes in certain solvents, such as methanol, ethanol, and THF, together with other alkoxysilanes and precursors as organic chain formers by water with hydrochloric acid as catalyst. The membrane manufacture process has been described in our former invention disclosures or patent applications (e.g. U.S. Prov. Pat. App. Ser. No. 60/439,985, filed Jan. 14, 2003). To enhance the proton conductivity of the membranes in low humidity environments, these polymers or copolymers shown in Scheme 6 can absorb acids, including, but not limited to, $H_3PO_4$, $HSO_4$, $CF_3SO_2NHSO_2CF_3$, $CF_3SO_3H$, $CH_3SO_3H$, $CF_3PO_3H_2$, and others.

Fluorinated Imidazole Ring Containing Precursors

Scheme 7 shows a general structure for fluorinated-imidazole-ring containing precursors for polymers or copolymers, where the functional group B for polymerization may be a group such as, but not limited to, an alkene group (—CR═CR'R"), epoxy group (—CR(O)CR'R"), or perfluoroalkene group (—CF═CF₂). Specific examples of such precursors include: 2-(but-3-enyl)-5-fluoro-1H-imidazole, 5-fluoro-4-(2-(oxiran-2-yl)ethyl)-1H-imidazole, 5-fluoro-4-(2,2,3,4,4-pentafluorobut-3-enyl)-1H-imidazole.

Scheme 7-1

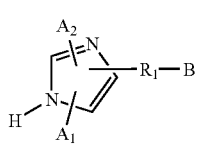

Scheme 7-2

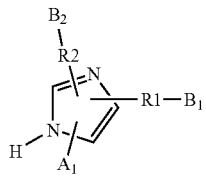

Scheme 7 above illustrates example fluorinated-imidazole-ring containing precursors for polymers or copolymers. Here, $A_1$ and $A_2$ can be —H, —F, —$CF_3$, and —$C_2F_5$ groups, where at least one of $A_1$ and $A_2$ is —F or a fluorine-containing group; $R_1$, $R_2$ is a linear organic chain with $C_1$ to $C_{20}$ (1-20 carbon atoms); and B, $B_1$, and $B_2$ is a functional group (such as a polymerizable group).

Synthesis of Fluorinated Imidazole Containing Monomers and Polymers

The examples below illustrate possible synthesis methods to obtain fluorinated-imidazole-ring containing precursors for polymers or copolymers.

The precursors were synthesized from 1H-imidazole-4-chloromethyl-5-fluoro-ethyl ester or 1H-imidazole-4-chloromethyl-2,5-fluoro-ethyl ester which were synthesized from 1H-imidazole-4-carboxylic-5-amino-ethyl ester. In some cases, chemicals were obtained from the Zelinsky Institute. The synthesis method was described in J. Am. Chem. Soc. 95(14), 4619-24, 1973, and in J. Org. Chem. 49(11), 1951-54, 1984. Several specific exemplary precursors were synthesized as follows.

EXAMPLE 1

Synthesis of 2-(3-butenyl)-4-(trifluoromethyl)-1H-Imidazole (Scheme 8)

In a solution of 3-dimethylhydrazone-1,1,1-trifluoro-2-propanone (1 mmol) and $NH_4OAc$ (1 mmol) in MeOH (6 ml), 4-pentenal (2 mmol) was added. The mixture was stirred for 1 h at room temperature, and then, at 50° C. for 48 hours. After cooling, 100 ml $CH_2Cl_2$ was added, and washed with saturated $Na_2CO_3$ solution. The solvent was removed in vacuum. The residual was separated with silica gel column (benzene/AcOEt=1/1). Yield: ~50%.

Scheme 8

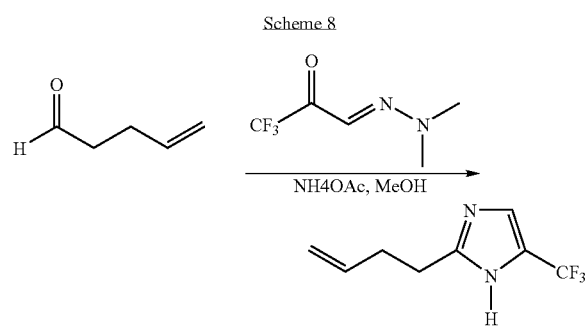

EXAMPLE 2

Polymerization of 2-(2,6-dimethyl-5-heptenyl)-4-(trifluoromethyl)-1H-imidazole (Scheme 9)

To a flask fitted with a stir-bar were added 2 g of 2-(2,6-dimethyl-5-heptenyl)-4-(trifluoromethyl)-1H-imidazole (synthesized with the method as described in J. Org. Chem., 1988, 53, 129), 10 mg of AIBN and 10 ml of DMF, The solution was degassed and placed in an oil bath at 70° C. for 3 h. The material was removed and the solvent removed by evacuation to yield the product polymer. To form the polymer membrane, the polymer was re-dissolved in DMF and cast to the Teflon plate, followed by drying at T=80° C. in the oven. The proton conductivity was from $10^{-5}$ S/cm to $10^{-3}$ S/cm in the range 80° C. to 160° C. in an anhydrous state.

Scheme 9

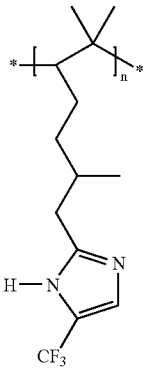

EXAMPLE 3

Polymerization of 2-(3-butenyl)-4-(trifluoromethyl)-1H-imidazole (Scheme 10)

To a flask fitted with a stir-bar were added 2 g of 2-(3-butenyl)-4-(trifluoromethyl)-1H-imidazole, 10 mg of AIBN and 10 ml of DMF. The solution was degassed and placed in an oil bath at 70° C. for 3 h. The material was removed and the solvent removed by evacuation to yield the product polymer. To form the polymer membrane, the polymer was re-dissolved in DMF and cast to the Teflon plate, followed by drying at T=80° C. in the oven. The proton conductivity was from $10^{-5}$ S/cm to $10^{-3}$ S/cm in the range 80° C. to 160° C. in an anhydrous state.

Scheme 10

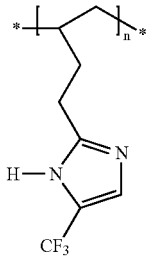

EXAMPLE 4

Copolymerization of 2-(3-butenyl)-4-(trifluoromethyl)-1H-imidazole and Dimethyl perfluoro(3-vinyloxypropyl)phosphonates (Scheme 11)

To a flask fitted with a stir-bar were added 2 g of 2-(3-butenyl)-4-(trifluoromethyl)-1H-imidazole, 3 g of dimethyl perfluoro(3-vinyloxypropyl)phosphonate, 25 mg of AIBN and 10 ml of 1,1,2-trichloro-1,2,2-trifluoroethane. The solution was degassed and placed in an oil bath at 70° C. for 20 h. The material was removed and the solvent removed by evacuation to yield the product polymer. To hydrolyze the —PO(OCH$_3$)$_2$ groups to —PO$_3$H$_2$, condensed HCl solution (50 ml) was mixed with the polymer and the resulting mixture was stirred at T=90° C. for 12 h. HCl solution was removed by evaporation under the vacuum. To form the polymer membrane, the polymer was re-dissolved in DMF and cast to the Teflon plate, followed by drying in the oven. The proton conductivity is from $10^{-4}$ S/cm to $10^{-2}$ S/cm from 80° C. to 160° C. in anhydrous state.

Scheme 11

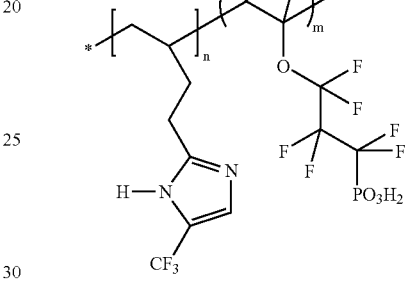

Synthesis of Immobilized Heterocycles

EXAMPLE 5

Synthesis of 5-(4-(3H-1,2,3-triazol-4-ylthio)butylthio)-1H-1,2,3-triazole (Scheme 12)

20 mmole of 5-mercapto-1H-1,2,3-triazole (sodium salt) was dissolved in 20 ml of ethanol in stirring. 10 mmole of 1,4-diiodobutane was added dropwise to the solution of 5-mercapto-1H-1,2,3-triazole (sodium salt), and stirred overnight. After the solvent was evaporated in vacuum, the residual was washed with 50 ml pure H$_2$O for three times, and then with 50 ml hexane for 3 times. At last, the residual was dried in oven at 60° C. for 24 hours. 1.8 g product was obtained as white solid. Yield: 70%. $^1$H NMR (DMSO): δ (ppm) 7.86 (2H, s), 2.85 (4H, m), and 1.66 (4H, m).

Scheme 12

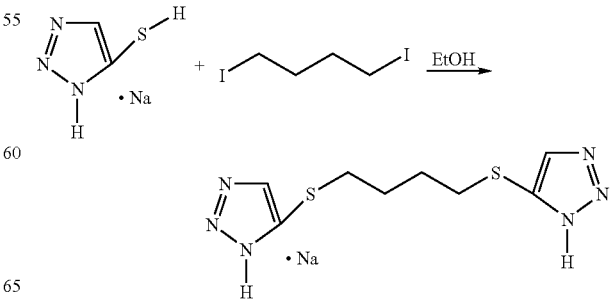

EXAMPLE 6

5-(8-(3H-1,2,3-triazol-4-ylthio)octylthio)-1H-1,2,3-triazole (Scheme 13)

20 mmole of 5-mercapto-1H-1,2,3-triazole (sodium salt) was dissolved in 20 ml of ethanol in stirring. 10 mmole of 1,8-diiodooctane was added dropwise to the solution of 5-mercapto-1H-1,2,3-triazole (sodium salt), and stirred overnight. After the solvent was evaporated in vacuum, the residual was washed with 50 ml pure $H_2O$ for three times, and then with 50 ml hexane for 3 times. At last, the residual was dried in oven at 60° C. for 24 hours. 1.30 g product was obtained as white solid. Yield: 42%. $^1$H NMR (DMSO): δ (ppm) 7.88 (2H, s), 2.86 (4H, t, $J_{H-H}$=7.14), 1.50 (4H, m), and 1.20-1.31 (8H, m).

Scheme 13

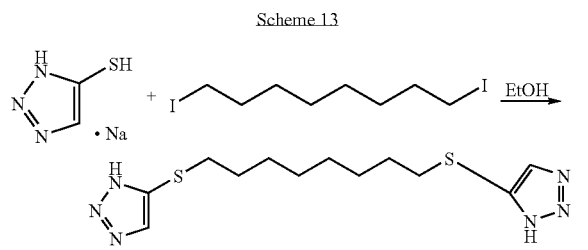

EXAMPLE 7

Synthesis of 3-(8-(1H-1,2,4-triazol-3-ylthio)octylthio)-1H-1,2,4-triazole (Scheme 14)

20 mmole of 3-mercapto-1H-1,2,4-triazole (potassium salt) was dissolved in 20 ml of ethanol in stirring. 10 mmole of 1,8-diiodooctane was added dropwise to the solution of 3-mercapto-1H-1,2,4-triazole (potassium salt), and stirred overnight. After the solvent was evaporated in vacuum, the residual was washed with 50 ml pure $H_2O$ for three times, and then with 50 ml hexane for 3 times. At last, the residual was dried in oven at 60° C. for 24 hours. 1.1 g product was obtained as white solid. Yield: 30%. $^1$H NMR (DMSO): δ(ppm) 8.34 (2H, s), 3.04 (4H, t, $J_{H-H}$=7.14), 1.61 (4H, m), and 1.23-1.32 (8H, m).

Scheme 14

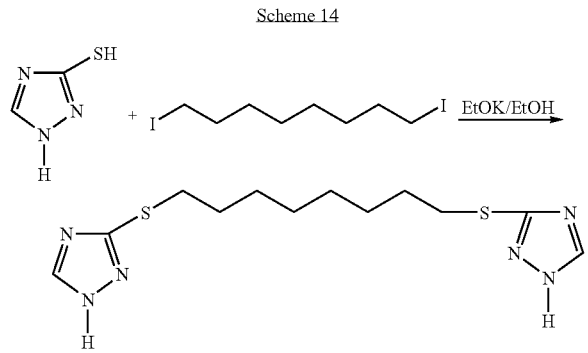

EXAMPLE 8

Synthesis of 1,2-bis(2-(3H-1,2,3-triazol-4-ylthio)ethoxy)ethane (Scheme 15)

10 ml of 1,2-bis(2-iodoethoxy)-ethane was dropped into the solution of 20 mmole 5-mercapto-1H-1,2,3-triazole (sodium salt) in 20 ml ethanol, and stirred for 24 hours at room temperature. After the solvent was evaporated in vacuum, the residual was separated with silica gel column. Elution with hexane/ethylacetate (1/3) first, and then with pure ethyl acetate gave 2.70 g product as viscous solid. Yield: 88%. $^1$H NMR (CDCl$_3$): δ(ppm) 7.72 (2H, s), 3.74 (4H, t, $J_{H-H}$=6.19), 3.65 (4H, s), 3.07 (4H, t, $J_{H-H}$=6.19).

Scheme 15

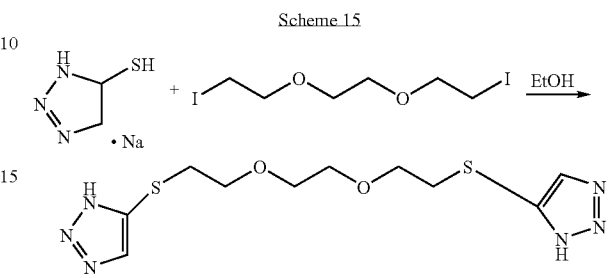

EXAMPLE 9

Synthesis of 2-(4-(pyrimidin-2-ylthio)butylthio)pyrimidine

Scheme 16

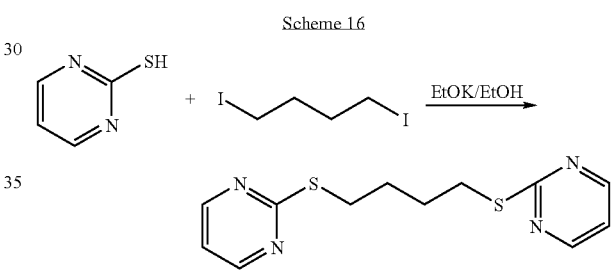

20 mmole of 2-mercaptopyrimidine was dissolved in 20 ml of ethanol with stirring. 20 mole of EtOK (24 weight % in ethanol) was added to the solution, stirred for 5 minutes. Then, about 10 mmole of 1,4-diiodobutane was added, and stirred overnight. The white precipitate was removed by filtration, the solvent in the filtrate was removed in vacuum. The obtained solid was dissolved in $CH_2Cl_2$, and separated with a Si gel column (solvents: 1 ethylacetate/1 hexane in volume). Yield: 86%. $^1$H NMR (CDCl$_3$) of PyrC4: δ(ppm) 8.50 (4H, d, $J_{H-H}$=4.77), 6.94 (2H, t, $J_{H-H}$=4.77), 3.20 (4H, t, $J_{H-H}$=6.93), and 1.91 (4H, t, $J_{H-H}$=6.93).

EXAMPLE 10

Synthesis of 4-(4-((1H-1,2,3-triazol-4-ylthio)methyl)benzylthio)-1H-1,2,3-triazole (Scheme 17)

20 mmole of 4-mercapto-1H-1,2,3-triazole (sodium salt) was dissolved in 20 ml of ethanol in stirring. 10 mole of 1,4-bis(chloromethyl)benzene in 20 ml ethanol was added dropwise to the solution of 4-mercapto-1H-1,2,3-triazole (sodium salt), and stirred overnight. The white precipitate was separated by filtration, and washed with 10 ml pure water for 3 times. The produced solid was dry at 60° C. for 6 hours, and 2.8 g product was obtained. Yield: 92%. $^1$H NMR (DMSO) of 3TriAr: δ(ppm) 7.75 (2H, s), 7.14 (4H, s), and 4.09 (4H, s).

Scheme 17

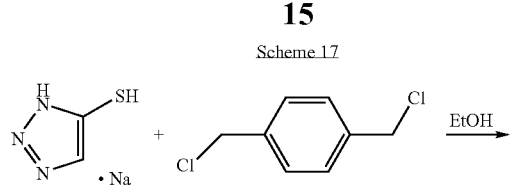

EXAMPLE 11

About 30 mmole of triethylamine was added dropwise to the mixture of 20 mmole of 3-mercapto-1H-1,2,4-triazole in 20 ml ethanol, and stirred until clear solution was obtained. 10 mole of 1,4-bis(chloromethyl)benzene in 20 ml ethanol was added dropwise to the above solution, and stirred overnight. The white precipitate was separated by filtration, and washed with 10 ml pure water for 3 times. The produced solid was dry at 60° C. for 6 hours, and 2.1 g white powder as product was obtained. Yield: 69%. $^1$H NMR (DMSO) of 4TriAr: δ(ppm) 8.50 (2H, s), 7.25 (4H, s), and 4.27 (4H, s).

Scheme 18

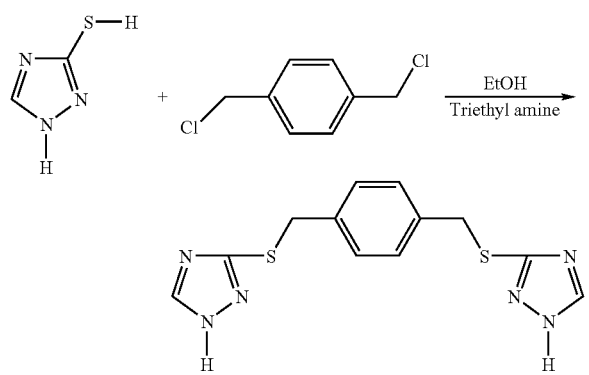

Synthesis of Heterocycle Grafted Precursors

Heterocycle-containing precursors, useful for preparation of polymers or copolymers, can include a linear organic chain with $C_1$ to $C_{20}$, and a functional group for polymerization. An example functional group for polymerization may include, but is not limited to, alkene group (—CR=CR'R"), epoxy group (—CR(O)CR'R"), perfluoroalkene group (—CF=CF$_2$). Specific examples of such precursors include: 5-fluoro-3-vinyl-1H-pyrazole, 4-(allyloxy)-2,3,5,6-tetrafluoropyridine, 4-(but-3-enyl)-2-fluoropyridine, 2-(but-3-enyl)pyrazine, 2-(but-3-enyl)-6-fluoropyrazine, 2-(allylthio)-4-fluoropyrimidine, 2-(allylthio)pyrimidine, 1-allyl-1H-[1,2,3]triazole.

EXAMPLE 12

Synthesis of 5-(4-vinylbenzylthio)-1H-1,2,3-triazole (Scheme 19)

10 mmole of 4-mercapto-1H-1,2,3-triazole (sodium salt) was dissolved in 20 ml of ethanol in stirring. 10 mmole of 4-vinylbenzene chloride was added, and stirred overnight. The precipitate was removed by filtration, the solvent in the filtrate was removed in vacuum. The obtained solid was separated with a Si gel column (solvents: 1 ethylacetate/1 hexane in volume). 2.1 g product was obtained. $^1$H NMR (CD$_3$Cl): 7.46 (1H, s), 7.31 (2H, d, $J_{H-H}$=8.16), 7.18 (2H, d, $J_{H-H}$=8.16), 6.67 (1H, m), 5.71 (1H, d, $J_{H-H}$=16.68), 5.22 (1H, d, $J_{H-H}$=11.68), 4.09 (2H, S).

Scheme 19

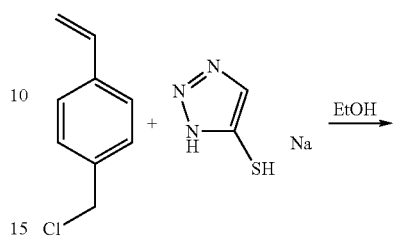

EXAMPLE 13

Synthesis of 2-(4-vinylbenzylthio)pyrimidine 10 mmole of 2-mercaptopyrimidine was dissolved in 20 ml of ethanol in stirring. 10 mole of EtOK was added to the solution, stirred for 5 minutes. Then, 10 mmole of 4-vinylbenzene chloride was added, and stirred overnight. The white precipitate was removed by filtration, the solvent in the filtrate was removed in vacuum. The obtained liquid was separated with a Si gel column (solvents: 1 ethylacetate/3 hexane). 2.1 g product was obtained. Yield: 92%. $^1$H NMR (CD$_3$Cl): 8.51 (2H, d, $J_{H-H}$=4.60), 7.38 (4H, m), 6.94 (1H, t, $J_{H-H}$=4.60), 6.68 (1H, m), 5.70 (1H, d, $J_{H-H}$=17.58), 5.21 (1H, d, $J_{H-H}$=10.95), 4.40 (2H, s).

Scheme 20

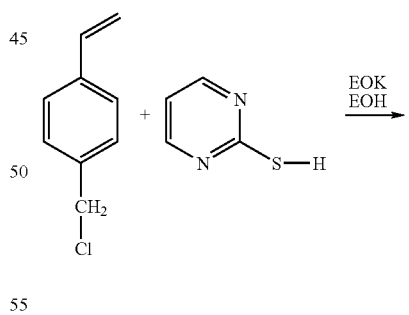

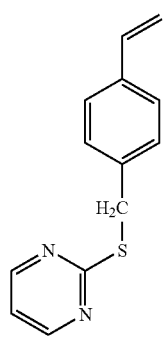

EXAMPLE 14

Synthesis of 3-(4-vinylbenzylthio)-1H-1,2,4-triazole (Scheme 21)

10 mmole of 1H-1,2,4-triazole-3-thiol was dissolved in 20 ml of ethanol in stirring. 10 mole of EtOK was added to the solution, stirred for 5 minutes. Then, 10 mmole of 4-vinylbenzene chloride was added, and stirred overnight. The white precipitate was removed by filtration, the solvent in the filtrate was removed in vacuum. The filtrate was separated with a Si gel column (solvents: 4 ethylacetate/hexane). 1.79 g product as white solid was obtained. Yield: 83%. $^1$H NMR (CD$_3$Cl): 8.73 (1H, s), 7.36 (4H, m), 6.75 (1H, m), 5.85 (1H, d, $J_{H-H}$=17.66), 3.25 (1H, d, $J_{H-H}$=10.93), 4.31 (2H, S).

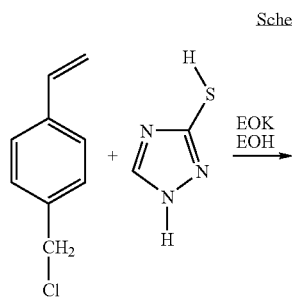

Scheme 21

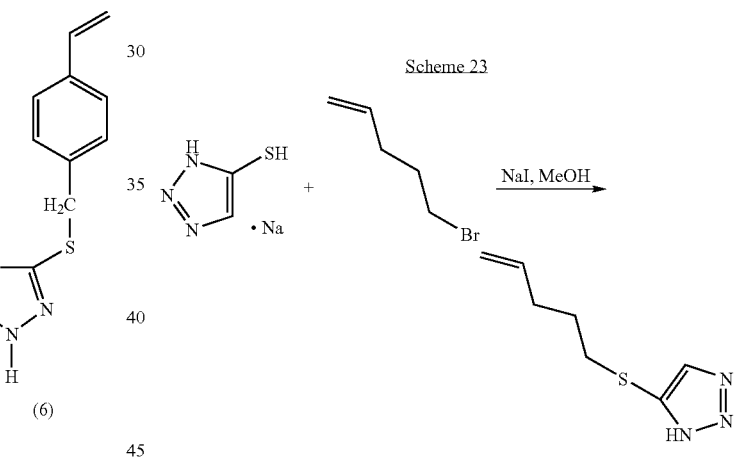

(6)

EXAMPLE 15

Synthesis of 2-(allylthio)pyrimidine (Scheme 22)

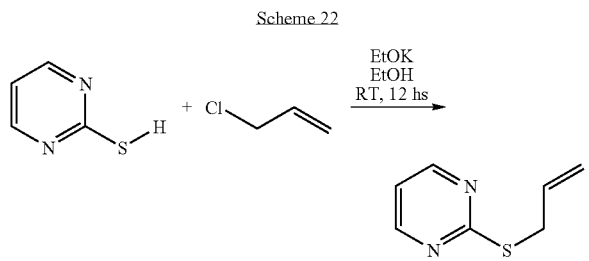

Scheme 22

10 mmole of 2-mercaptopyrimidine was dissolved in 20 ml of ethanol in stirring. 10 mole of EtOK was added to the solution, stirred for 5 minutes. At last, about 20 mmole (Not more than 30 mmole) of 3-chloropropylene was added, and stirred overnight. The white precipitate was removed by filtration, the solvent in the filtrate was removed in vacuum. The obtained viscous liquid was separated with a Si gel column (solvents: 1 ethylacetate/3 hexane). $^1$H NMR (CD$_3$Cl): δ(ppm) 8.39 (2H, d, $J_{H-H}$=4.74), 6.86 (1H, t, $J_{H-H}$=4.74), 5.89 (1H, m), 5.20 (1H, d, $J_{H-H}$=17.00), 5.00 (1H, d, $J_{H-H}$=9.97), 3.71 (2H, d, $J_{H-H}$=6.83). Yield: 90%.

EXAMPLE 16

Synthesis of 5-(pent-4-enylthio)-1H-1,2,3-triazole 5-bromopent-1-ene (10 mmol) and NaI were dissolved in 30 ml MeOH and stirred at room temperature for 12 h. 10 mmol 5-mercapto-1H-1,2,3-triazole (sodium salt) was added to above solution and further stirred for 24 hours. After the solvent MeOH was evaporated in vacuum, a mixture of hexane and ethyl acetate (1/1 in volume) 100 ml was added and stirred for 5 minutes. The precipitate was removed by filtration. The solvent in the filtrate was removed in vacuum. The residual was separated with a Si gel column (solvents: 1 ethyl acetate/1 hexane in volume). 0.8 g product was obtained as colorless oil. Yield: 47%. $^1$H NMR (CDCl$_3$): 11.14 (1H, brs.), 7.69 (1H, s), 5.77 (1H, m), 5.03 (2H, m), 2.95 (2H, t), 2.17 (2H, m), 1.74 (2H, m).

Scheme 23

EXAMPLE 17

Synthesis of 3-(pent-4-enylthio)-1H-1,2,4-triazole 5-bromopent-1-ene (10 mmol) and NaI were dissolved in 30 ml MeOH and stirred at room temperature for 12 h. 10 mmol 3-mercapto-1H-1,2,4-triazole (potassium salt) in 10 ml MeOH was added to above solution and further stirred for 24 hours. After the solvent MeOH was evaporated in vacuum, a mixture of hexane and ethyl acetate (1/1 in volume) 100 ml was added and stirred for 5 minutes. The precipitate was removed by filtration. The solvent in the filtrate was removed in vacuum. The residual was separated with a Si gel column (solvents: 1 ethyl acetate/1 hexane in volume). 1.2 g product was obtained as colorless oil. Yield: 71%. $^1$H NMR (CDCl$_3$): 10.83 (1H, brs.), 8.17 (1H, s), 5.75 (1H, m), 4.99 (2H, m), 3.16 (2H, t), 2.19 (2H, m), 1.82 (2H, m).

Scheme 24

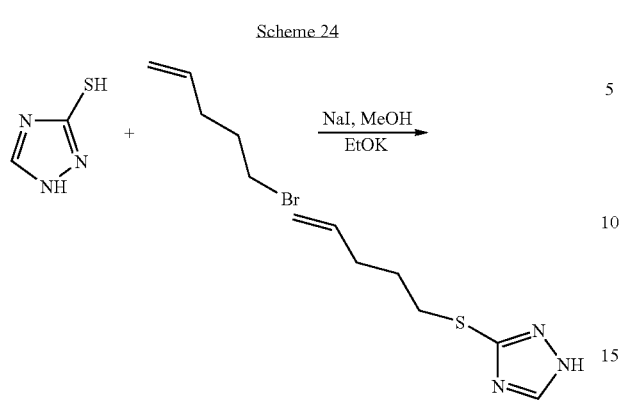

EXAMPLE 18

Synthesis of 4-(allyloxymethyl)-1H-1,2,3-triazole

Scheme 25

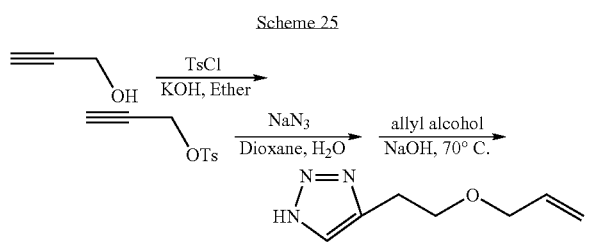

200 mmol propargyl alcohol and 500 mmol NaOH were mixed with 60 ml Ether and 20 ml H$_2$O, cooled by ice bath. 190 mmol p-toluenesulfonyl chloride was slowly added to the solution. After stirred for 1 h, the resulted mixture was washed with water, separated and evaporated under reduced pressure. 180 mmol tosylated allyl alcohol was achieved.

50 mmol tosylated allyl alcohol mixed with 60 mmol sodium azide in 15 ml dioxane and 3 ml water, were stirred at room temperature overnight. Allyl alcohol (17 ml) and sodium hydroxide (150 mmol) were then added into the solution and stirred at 70° C. overnight. The resulting solution was neutralized using concentrated HCl. After evaporation under reduced pressure, acetone was added and salts were removed by filtration. The resulted mixture was distilled. At 150° C., 0.2 torr, 10 mmol 4-(allyloxymethyl)-1H-1,2,3-triazole was achieved.

EXAMPLE 19

Synthesis of (1-(4-methoxybenzyl)-1H-1,2,3-triazole-4-yl)methanol

Scheme 26

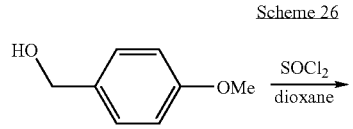

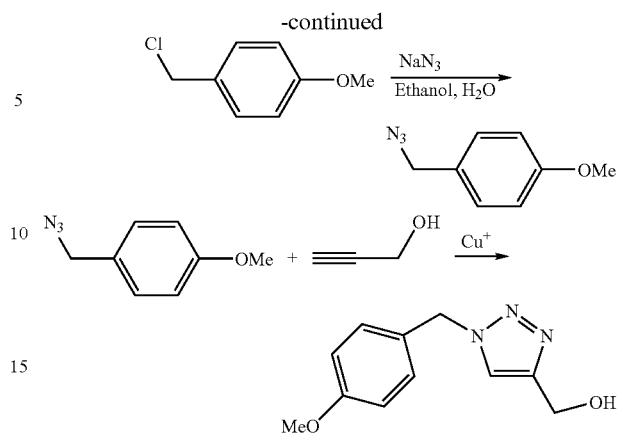

110 mmol 4-methoxybenzyl alcohol was dissolved in 60 ml dioxane and 150 mmol SOCl$_2$ was slowly dropped into the solution. The solution was stirred for 3 h at 60° C. and evaporated under reduced pressure. EtOAc was added and the resulted solution was washed with water. The separated organic layer was dried and evaporated to give 107 mmol 1-(chloromethyl)-4-methoxybenzene.

64 mmol 1-(chloromethyl)-4-methoxybenzene and 90 mmol sodium azide were dissolved in 20 ml ethanol and 5 ml water, and stirred overnight at room temperature. CH$_2$Cl$_2$ and water were added. The organic layer was separated, dried and evaporated to give 48 mmol 1-(azidomethyl)-4-methoxybenzene.

93 mmol 1-(azidomethyl)-4-methoxybenzene, 110 mmol propargyl alcohol were mixed in 230 ml tert-butyl alcohol/H$_2$O (1:1) solution. 1 mmol CuSO$_4$.5H$_2$O and 10 mmol Ascorbic acid sodium salts dissolved in 2 ml water were added into the solution. The mixture was stirred for 2 days. After evaporation, the mixture was purified by flash column to give 55 mmol (1-(4-methoxybenzyl)-1H-1,2,3-triazole-4-yl) methanol. $^1$H NMR (CDCl$_3$): 7.42 (1H, s), 7.22 (2H, d, J$_{H-H}$=8.70), 6.88 (2H, d, J$_{H-H}$=8.70), 5.43 (2H, s), 4.73 (2H, s), 3.79 (3H, s).

EXAMPLE 20

Synthesis of 1-(4-methoxybenzyl)-4-vinyl-1H-1,2,3-triazole

Scheme 27

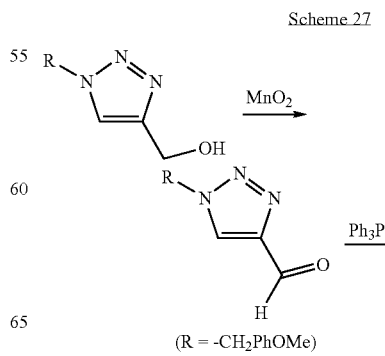

(R = -CH$_2$PhOMe)

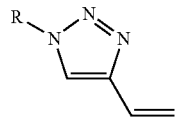

75 mmol (1-(4-methoxybenzyl)-1H-1,2,3-triazole-4-yl) methanol was dissolved in CH$_2$Cl$_2$. 150 mmol MnO$_2$ was added into the solution and the resulted mixture was stirred at room temperature for 3 days. After filtration, CH$_2$Cl$_2$ was removed by evaporation and 50 mmol 1-(4-methoxybenzyl)-1H-1,2,3-triazole-4-carbaldehyde was achieved. $^1$H NMR (CDCl$_3$): δ(ppm) 3.81 (3H, s), 5.51 (2H, s), 6.91 (2H, d, $J_{H-H}$=8.18), 7.25 (2H, d, $J_{H-H}$=8.18), 7.95 (1H, s), 10.10 (1H, s).

Methyltriphenylphosphonium bromide 6 mmol was dissolved in anhydrous THF 10 ml. Under nitrogen gas, at 0° C., n-butyl lithium (2M in cyclohexane) 3.5 ml was added into the solution and the mixture was stirred for 1 h at room temperature. 4.6 mmol 1-(4-methoxybenzyl)-1H-1,2,3-triazole-4-carbaldehyde in 5 ml THF was added into the solution and stirred overnight. The resulted mixture was purified by flash column and 4.6 mmol 1-(4-methoxybenzyl)-4-vinyl-1H-1,2,3-triazole was achieved. $^1$H NMR (CDCl$_3$): δ(ppm) 3.80 (3H, s), 5.30 (1H, d, $J_{H-H}$=), 5.51 (2H, s), 6.91 (2H, d, $J_{H-H}$=8.18), 7.25 (2H, d, $J_{H-H}$=8.18), 7.95 (1H, s), 10.10 (1H, s).

Synthesis of Heterocycle Grafted Alkoxysilanes

Heterocycle-containing precursors which may be used in the preparation hybrid inorganic-organic copolymers are shown in Scheme 7. Specific examples include: 2-(3-(trimethoxysilyl)propylthio)-pyrimidine, 2-(3-(trimethoxysilyl) propylthio)pyrimidine, and the like.

Scheme 28

Scheme 28: Heterocycle grafted polymers. R$_1$ can be a linear organic chain with C$_1$ to C$_{20}$; M can be alkoxy, such as C$_2$H$_5$— or CH$_3$O—; A can be alkyl, such as C$_2$H$_5$— or CH$_3$—; X is 1, 2, or 3; and y=1 or 2 (x+y=3).

The precursors were synthesized from 1H-imidazole-4-chloromethyl, 5-fluoro-ethyl ester or 1H-imidazole-4-chloromethyl, 2,5-fluoro-ethyl ester. Several specific exemplary precursors were synthesized as follows.

EXAMPLE 21

Synthesis of 5-(4-(2-(trimethoxysilyl)ethyl)benzylthio)-1H-1,2,3-triazole (Scheme 29).

10 mmole of 5-mercapto-1H-1,2,3-triazole (sodium salt) was dissolved in 20 ml methanol and stirred for 5 minutes. 10 mmole of ((chloromethyl)phenylethyl)-trimethoxysilane was added to the solution, and stirred for 6 hours. The white precipitate was removed by filtration, the solvent in the filtrate was removed in vacuum. The filtrate was dissolved in small amount of methanol, and separated with a Si gel column (solvents: 5 ethylacetate/5 hexane in volume). 2.2 g product as liquid was obtained. Yield: 64.8%. $^1$H NMR (CDCl$_3$) of Precursors 5: δ(ppm) 7.47 (1H, s), 7.12 (4H, m), 4.06 (2H, s), 3.55 (9H, s), 2.69 (2H, t, $J_{H-H}$=8.50), 1.00 (2H, t, $J_{H-H}$=8.50).

Scheme 29

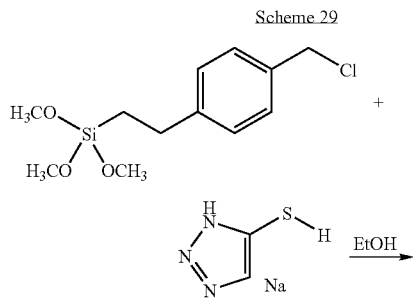

EXAMPLE 22

Synthesis of 3-(4-(2-(trimethoxysilyl)ethyl)benzylthio)-1H-1,2,4-triazole (Scheme 30)

10 mmole of 3-mercapto-1H-1,2,4-triazole was dissolved in 20 ml ethanol, then 10 mmole EtOK was added, and stirred for 5 minutes. 10 mmole of ((chloromethyl)phenylethyl)trimethoxysilane was added to the solution, and stirred for 6 hours. The white precipitate was removed by filtration, the solvent in the filtrate was removed in vacuum. The obtained solid was dissolved in methanol, and separated with a Si gel column (solvents: 7 ethylacetate/3 hexane in volume). Yield: 53%. $^1$H NMR (CDCl$_3$) of Precursors 6: δ(ppm) 8.09 (1H, s), 7.19 (4H, m), 4.29 (2H, s), 3.55 (9H, s), 2.72 (2H, t, $J_{H-H}$=8.50), 1.02 (2H, t, $J_{H-H}$=8.50).

Scheme 30

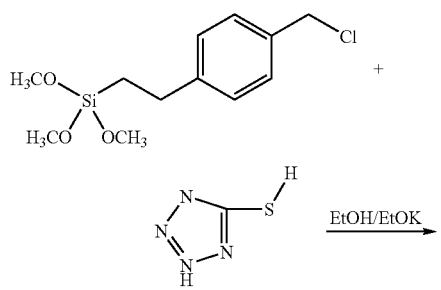

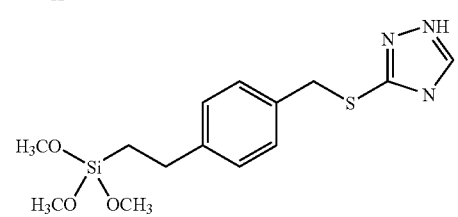

EXAMPLE 23

Synthesis of 4-((3-(diethoxy(methyl)silyl)propylthio)methyl)-2-fluoropyridine (Scheme 31)

Scheme 31

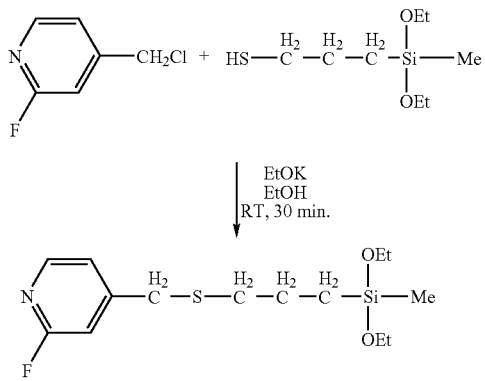

10 mmole of 3-mercaptopropylmethyldiethoxysilane was dissolved in 10 ml ethanol, then 10 mmole EtOK was added, and stirred for 5 minutes. 10 mmole of 2-fluoropyridine in 10 ml ethanol was added to the solution, and stirred for 30 minutes. The white precipitate was removed by filtration, the solvent in the filtrate was removed in vacuum. The product was purified with a short Si gel column. The solvent was 1:3 ethyl acetate:hexane by volume. $^1$H NMR (CD$_3$Cl): δ(ppm) 0.03 (3H, s), 0.60 (2H, m), 1.15 (6H, m), 1.55 (2H, m), 2.40 (2H, m), 3.65 (4H, m), 6.85 (1H, s), 7.09 (1H, d, J$_{H-H}$=5.02), 8.08 (1H, d, J$_{H-H}$=5.02. Yield: 78%.

EXAMPLE 24

Synthesis of 2-(4-(2-(trimethoxysilyl)ethyl)benzylthio)pyrimidine (Scheme 32)

10 mmole of 2-mercaptopyrimidine was dissolved in 20 ml ethanol, then 10 mmole EtOK was added, and stirred for 5 minutes. 10 mmole of ((chloromethyl)phenylethyl)trimethoxysilane was added to the solution, and stirred for 6 hours. The white precipitate was removed by filtration, the solvent in the filtrate was removed in vacuum. The obtained viscous liquid was separated with a Si gel column (solvents: 1 ethylacetate/3 hexane). $^1$H NMR (CD$_3$Cl): δ(ppm) 8.50 (2H, m, Pyr.-H), 7.25 (4H, m, Ar—H), 6.95 (1H, m, Pyr.-H), 4.38 (2H, s —CH$_2$—), 3.54 (9H, s, —CH$_3$), 2.70 (2H, m, —CH$_2$—), 0.99 (2H, m, —CH$_2$—). Yield: 73%.

Scheme 32

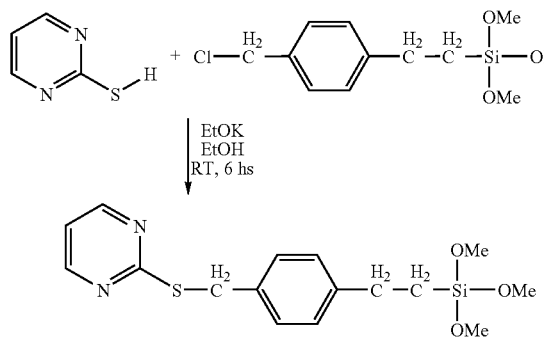

EXAMPLE 25

Synthesis of 2-(3-(trimethoxysilyl)propylthio)pyrimidine (Scheme 33)

2-(3-(trimethoxysilyl)propylthio)pyrimidine was synthesized from 2-mercaptopyrimidine and iodopropyltrimethoxysilane in the similar method as described above. $^1$H NMR (CD$_3$Cl): δ(ppm) 8.62 (2H, m, Pyr.-H), 7.11 (1H, m, Pyr.-H), 3.57 (9H, s, —CH$_3$), 3.25 (2H, m, —CH$_2$—), 1.88 (2H, m, —CH$_2$—), 0.83 (2H, t, J$_{H-H}$=8.25, —CH$_2$—). Yield: 74%.

Scheme 33

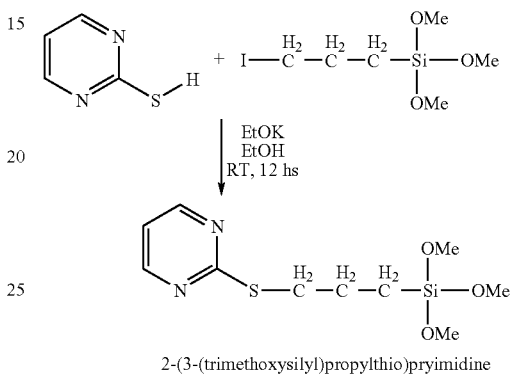

2-(3-(trimethoxysilyl)propylthio)pryimidine

Synthesis of Polymers, Copolymers, and Hybrid Inorganic-Organic Copolymer Membranes

EXAMPLE 26

Polymerization of 1-(4-methoxybenzyl)-4-vinyl-1H-1,2,3-triazole

Scheme 34

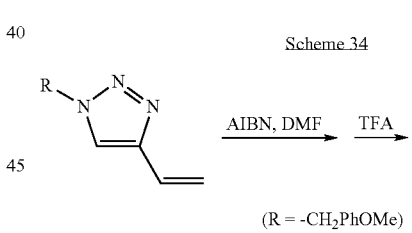

(R = -CH$_2$PhOMe)

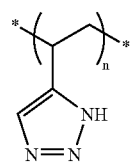

4.6 mmol 1-(4-methoxybenzyl)-4-vinyl-1H-1,2,3-triazole and 0.05 mmol AIBN were dissolved in 2 ml DMF. The polymerization were performed at T=65° C. overnight. After polymerization, the solvent was removed under reduced pressure. Then 15 ml TFA was added and the mixture was heat at 70° C. for 10 hours. After evaporation and washed with ethyl acetate several times, polymers (4.5 mmol in monomer) were achieved. $^1$H NMR (DMSO-d$_6$): δ(ppm) 2.13-2.22 (—CH$_2$CH—), 7.34-7.56 (N—CH).

FIG. 1 shows the proton conductivity of poly(4-vinyl-1H-1,2,3-triazole) in dir air from room temperature to 120° C., compared with poly(4-vinyl-1H-imidazole) from *Solid State Ion.* 138, 259-265 (2001).

EXAMPLE 27

Synthesis of poly(2-(4-vinylbenzylthio)pyrimidine), Scheme 35

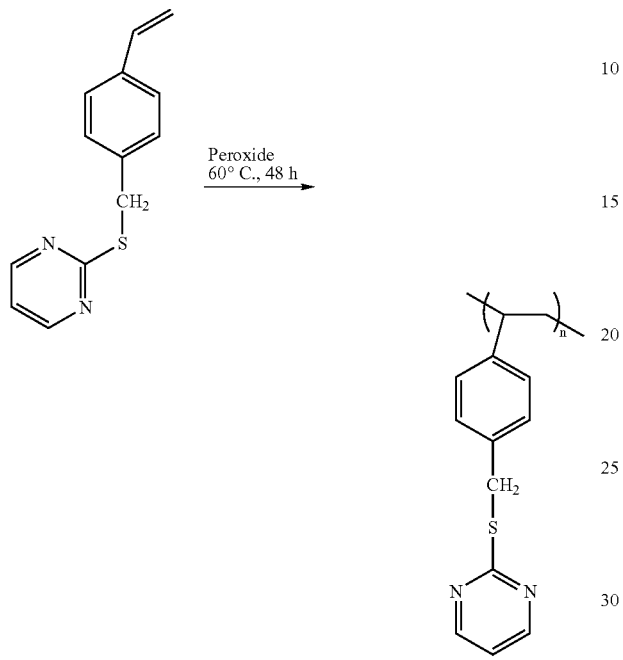

EXAMPLE 28

Synthesis of Poly (5-(4-vinylbenzylthio)-1H-1,2,3-triazole), Scheme 43

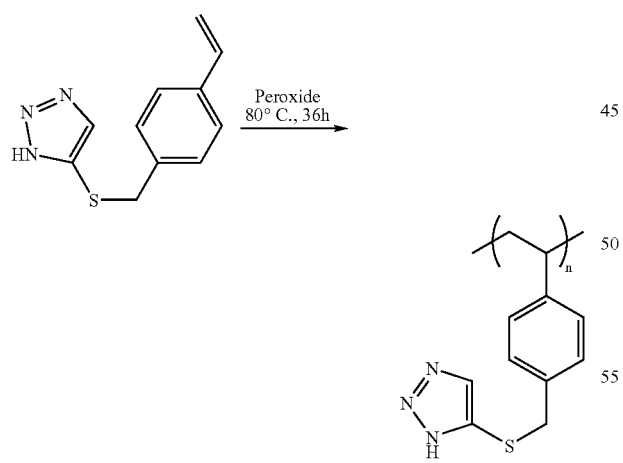

EXAMPLE 29

Composite Membranes of Sulfonated Polysulfone (s-PSU) and 1H-1,2,3-triazole

Sulfonated polysulfone (sPSU) was prepared by using chlorosulfonic acid in dichloroethane following the procedure of Johnson et al. (*J. Polym. Sci., Polym, Chem. Ed.* 1984, 22, 721). Excess chlorosulfonic acid was removed by washing products in the dichloroethane, ethanol and deionized water for several times. The sPSU was dried in the oven at 120° C. for two weeks over $P_2O_5$ and then kept in a desiccator. Ion-Exchange Capacity (IEC) of sPSU was determined by 1H NMR and back titration. The sPSU polymers (IEC of 1.40 mequiv/g) were immersed into various amount of liquid 1H-1,2,3-triazole at 90° C., which readily intercalated into the polymer thus producing homogeneous membranes. By weighing the polymer before and after mixed with 1H-1,2,3-triazole, the ratio n=[1H-1,2,3-triazole]/[—$SO_3H$] was calculated. All the samples were kept in a glove box dried with $P_2O_5$ in a nitrogen atmosphere.

Figure 2:
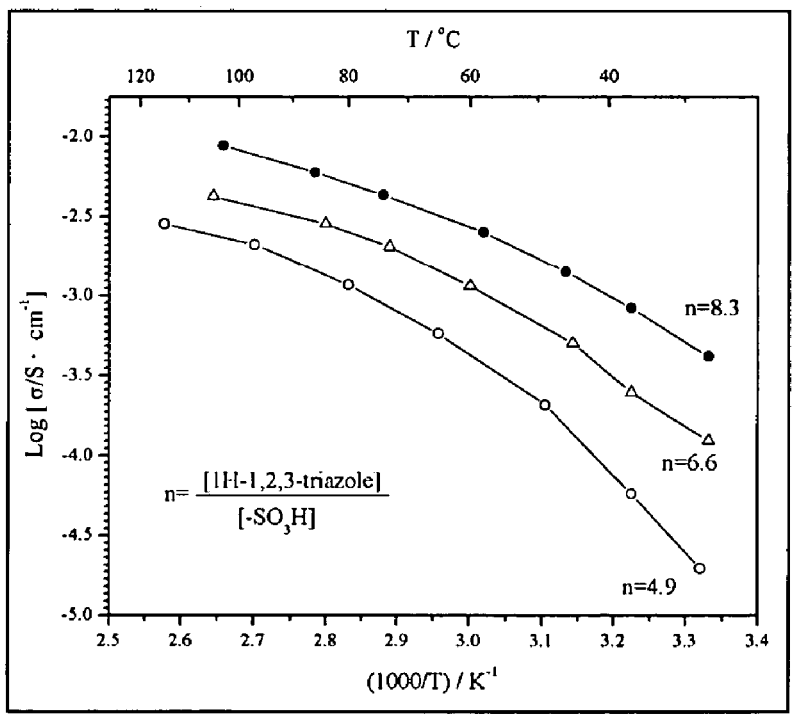
FIG. 2 shows proton conductivity of s-PSU doped with 1H-1,2,3-triazole in the anhydrous state.

FIG. 2 shows proton conductivity of s-PSU doped with 1H-1,2,3-triazole in anhydrous state. Proton conductivity of the materials is 0.01 S/cm at 120° C. and $10^{-4}$ S/cm at room temperature.

EXAMPLE 30

Composite Membranes of Sulfonated Polysulfone (s-PSU) and 1H-1,2,4-triazole

The sPSU polymers (IEC of 1.40 mequiv/g) were mixed into various amount of liquid 1H-1,2,4-triazole at 120° C., which readily intercalated into the polymer thus producing homogeneous membranes. By weighing the polymer before and after it was mixed with 1H-1,2,4-triazole, the ratio n=[1H-1,2,4-triazole]/[—$SO_3H$] was calculated. All the samples were kept in a glove box dried with $P_2O_5$ in a nitrogen atmosphere.

Figure 3:
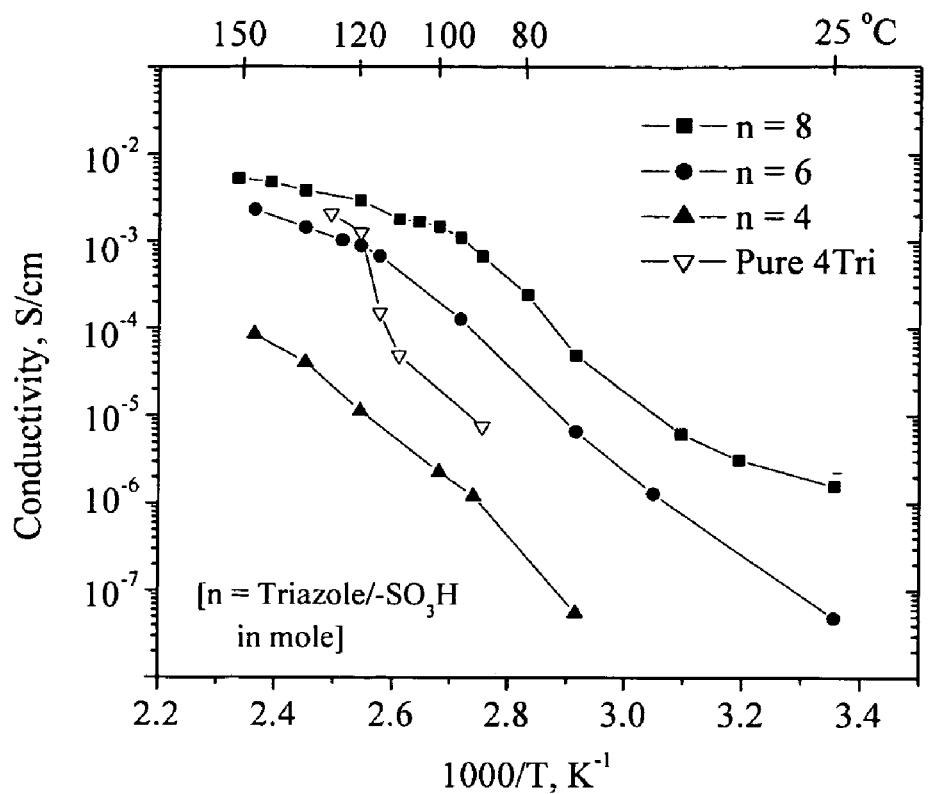
FIG. 3 shows ionic conductivities of 1H-1,2,4-triazole (4Tri) and that compound intercalated into sulfonated polysulfone polymers, where n is the mole ratio of triazole-ring/—$SO_3H$.

FIG. 3 shows proton conductivity of s-PSU doped with 1H-1,2,4-triazole in anhydrous state. Proton conductivity of the materials is $5 \times 10^{-3}$ S/cm at 140° C. and $1.5 \times 10^{-3}$ S/cm at 100° C.

EXAMPLE 31

Composite Materials of 4TriC4 (see Scheme 37) and 4-dodecylbenzenesulfonic Acid ($C_{12}PhSO_3H$) were Prepared

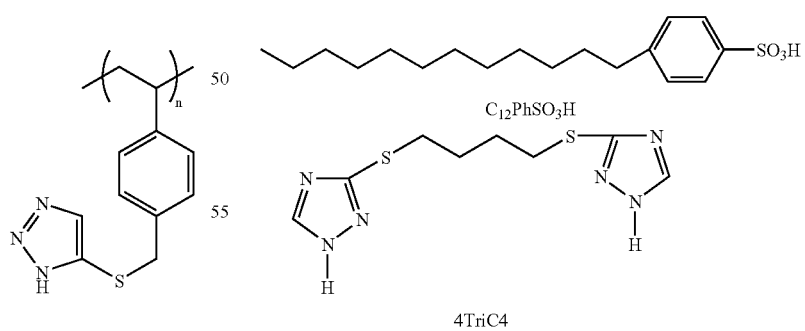

The mixtures of 4TriC4 and $C_{12}PhSO_3H$ were made by co-dissolved in methanol in stirring, and then evaporating the solvents in vacuum at 80° C. The mixtures were sealed in an glass bottle for proton conductivity.

Figure 4:
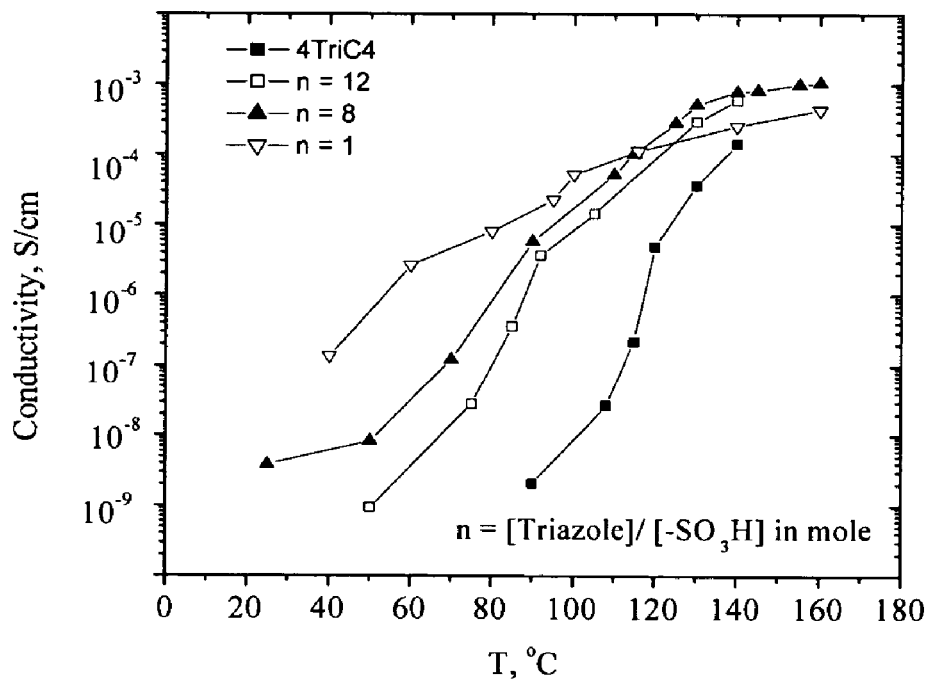
FIG. 4 shows proton conductivity of the mixtures of immobilized 1H-1,2,4-triazole (4TriC4) and large molecule acid $C_{12}PhSO_3H$ in the anhydrous state.

FIG. 4 presents the proton conductivity of the mixtures of 4TriC4 and $C_{12}PhSO_3H$ in anhydrous state.

EXAMPLE 32

The conductivities of 1H-1,2,3-triazole doped with different types of acids and of different concentrations were measured at room temperature under anhydrous condition. The resulted mixture showed high ionic conductivity. The acids used included benzenesulfonic acid ($C_6H_5SO_3H$), sulfonic acid ($H_2SO_4$), dibenzenesulfonimide ($C_6H_5SO_2NHSO_2C_6H_5$), and phenylphosphonic acid ($C_6H_5PO_3H_2$).

Figure 5:
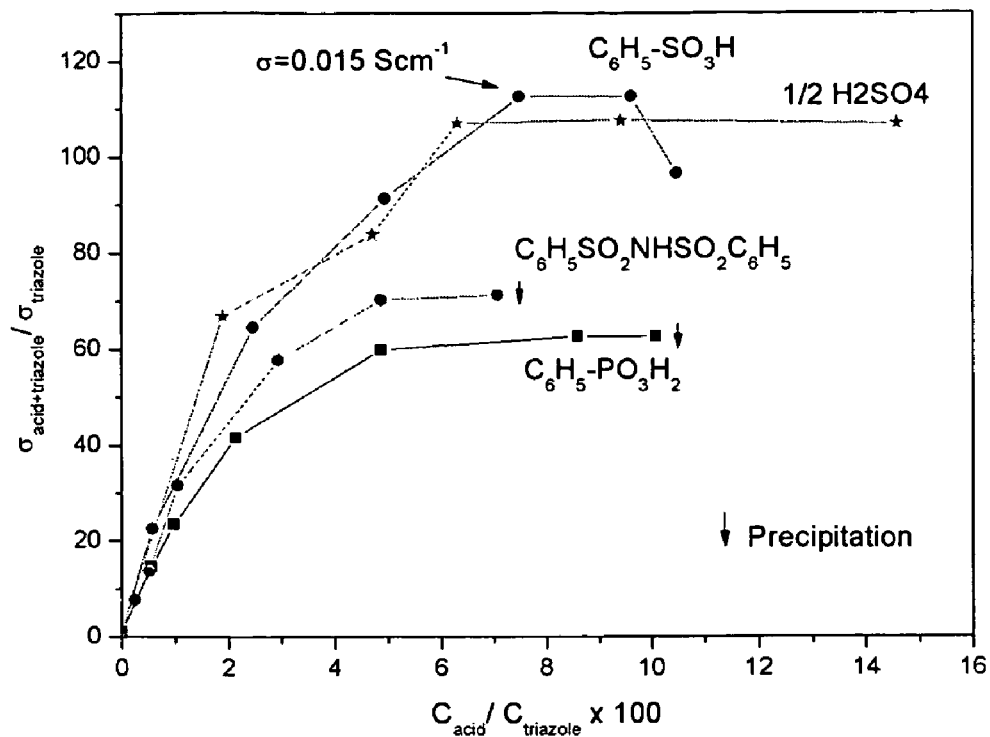
FIG. 5 shows the conductivity ratio of the acid-triazole mixture to the pure 1H-1,2,3-triazole ($\sigma_{triazole+acid}/\sigma_{triazole}$) against the concentration ratio of acid to the triazole ($C_{acid}/C_{triazole} \times 100$)

FIG. 5 shows the conductivity ratio of the acid-triazole mixture to the pure 1H-1,2,3-triazole ($\sigma_{triazole+acid}/\sigma_{triazole}$) against the concentration ratio of acid to the triazole ($C_{acid}/C_{triazole} \times 100$). As shown in FIG. 5, the highest conductivity of acid-triazole mixture is about 0.015 S/cm at room temperature under anhydrous condition.

EXAMPLE 33

Hybrid Inorganic-Organic Copolymer Membranes with Grafted 1H-1,2,4-triazole and Phosphonic Acid 3-(4-(2-(trimethoxysilyl)ethyl)benzylthio)-1H-1,2,4-triazole (Si4Tri), Bis((3-methyldimethoxysilyl)propyl)polypropylene oxide (MDSPPO), and tetraethoxysilane (TEOS) were dissolved in ethanol by stirring. 0.5 N HCl aqueous solution was added dropwise to the mixture, stirred for 24 hours, and then $H_3PO_4$ solution of ethanol was added dropwise with further stirring for 6 hours. The sols were cast on petri dishes. The amount of water added was 4 times of the total Si in mole.

The membranes were dried at 60° C. for 3 days, at 80° C. for 3 hours, and then at 100° C. for 1 hour to evaporate the organic solvents and water. The samples were labeled by their mole composition as x MDSPPO-y TEOS-z Si4Tri-m $H_3PO_4$, where x, y, and z represent the moles of Si from MDSPPO, TEOS, and Si4Tri, an m is the moles of $H_3PO_4$, respectively. The value of x is 1-2, y 2-4, z 3-6, and m 3-8. The proton conductivity varied from $10^{-7}$ S/cm to $10^{-2}$ S/cm from room temperature to 150° C. in anhydrous state.

Figure 6:
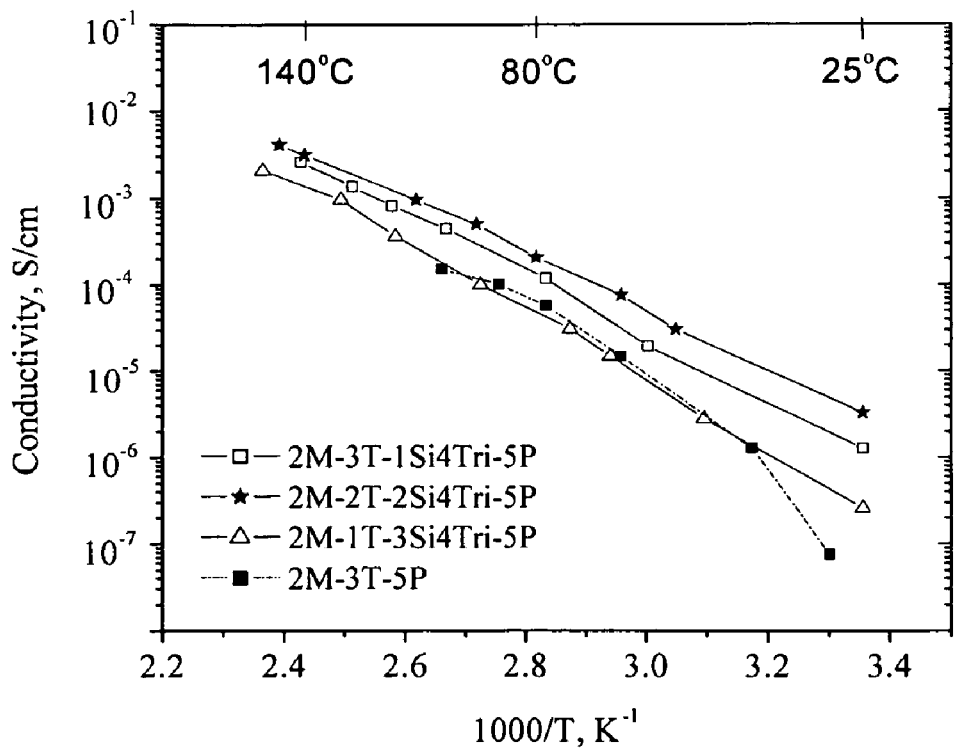
FIG. 6 shows proton conductivity of membranes x MDSPPO-y TEOS-z Si4Tri-m $H_3PO_4$ in anhydrous state.

FIG. 6 shows the proton conductivities of the membranes with compositions of 2 MDSPPO-y TEOS-z Si4Tri-5 $H_3PO_4$ (y=3, 2, and 1; z=1, 2, and 3) in anhydrous state, compared with those of the membrane without grafted heterocycles.

EXAMPLE 34

Hybrid inorganic-organic copolymer membranes with pyrimidine terminated side chain and —$SO_3H$ group terminated side chain: 3-(trihydroxysilyl)-1-propane sulfonic acid (S), 2-(4-(2-(trimethoxysilyl)ethyl)benzylthio)pyrimidine (SiPy), Bis((3-methyldimethoxysilyl)propyl)polypropylene oxide (M), and bis(triethoxysilyl)octane (Oc) were dissolved in ethanol by stirring. 0.5 N HCl aqueous solution was added dropwise to the mixture, and further stirred for 6 hours. At last the sols were cast on petri dishes. The water amount added is 4 times of the total Si in mole.

The membranes were dried at 60° C. for 3 days, at 80° C. for 3 hours, and then at 100° C. for 1 hour to evaporate the organic solvents and water. The samples were labeled by their mole composition as x M-y Oc-z SiPy-m S, where x, y, z, and m represent the moles of Si from M, Oc, PPr, and S, respectively. The value of x is 2-4, y 1-2, z 2-6, and m 2-6. These membranes are thermally stable up to 240° C. in dry air. The proton conductivity varied from $10^{-7}$ S/cm to $10^{-1}$ S/cm from room temperature to 160° C. in varying relative humidity.

EXAMPLE 35

Hybrid inorganic-organic copolymer membranes with 1H-1,2,3-triazole terminated side chain and —$SO_3H$ group terminated side chain: 3-(trihydroxysilyl)-1-propane sulfonic acid (S), 5-(4-(2-(trimethoxysilyl)ethyl)benzylthio)-1H-1,2,3-triazole (Si3Tri), bis((3-methyldimethoxysilyl)propyl) polypropylene oxide (M), and bis(triethoxysilyl)octane (Oc) were dissolved in ethanol by stirring. 0.5 N HCl aqueous solution was added dropwise to the mixture, and further stirred for 6 hours. Then, the sols were cast on petri dishes. The water amount added is 4 times of the total Si in mole. The membranes were dried at 60° C. for 3 days, at 80° C. for 3 hours, and then at 100° C. for 1 hour to evaporate the organic solvents and water. The samples were labeled by their mole composition as x M-y Oc-z Si3Tri-m S, where x, y, z, and m represent the moles of Si from M, Oc, Si3Tri, and S, respectively. The value of x is 2-4, y 1-2, z 2-6, and m 2-6. These membranes are thermally stable up to 240° C. in dry air. The proton conductivity is from $10^{-7}$ S/cm to $10^{-1}$ S/cm from room temperature to 160° C. in low relative humidity.

EXAMPLE 36

Hybrid inorganic-organic copolymer membranes with fluorinated pyridine terminated side chain and —$SO_3H$ group terminated side chain: 3-(trihydroxysilyl)-1-propane sulfonic acid (S), 4-((3-(diethoxy(methyl)silyl)propylthio)methyl)-2-fluoropyridine (SiFP), bis((3-methyldimethoxysilyl)propyl) polypropylene oxide (M), and bis(triethoxysilyl)octane (Oc) were dissolved in ethanol by stirring. Aqueous solution of 0.5 N HCl was added dropwise to the mixture, and further stirred for 6 hours. The sols were cast on petri dishes. The water amount added was 4 times of the total Si in mole. The membranes were dried at 60° C. for 3 days, at 80° C. for 3 hours, and then at 100° C. for 1 hour to evaporate the organic solvents and water. The samples were labeled by their mole composition as x M-y Oc-z SiFP-m S, where x, y, z, and m represent the moles of Si from M, Oc, SiFP, and S, respectively. In representative examples, the value of x is 2-4, y is 1-2, z is 2-6, and m is 2-6. These membranes are thermally stable up to 240° C. in dry air. The proton conductivity varied from $10^{-7}$ S/cm to $10^{-1}$ S/cm from room temperature to 160° C. in low relative humidity.

Figure 7:
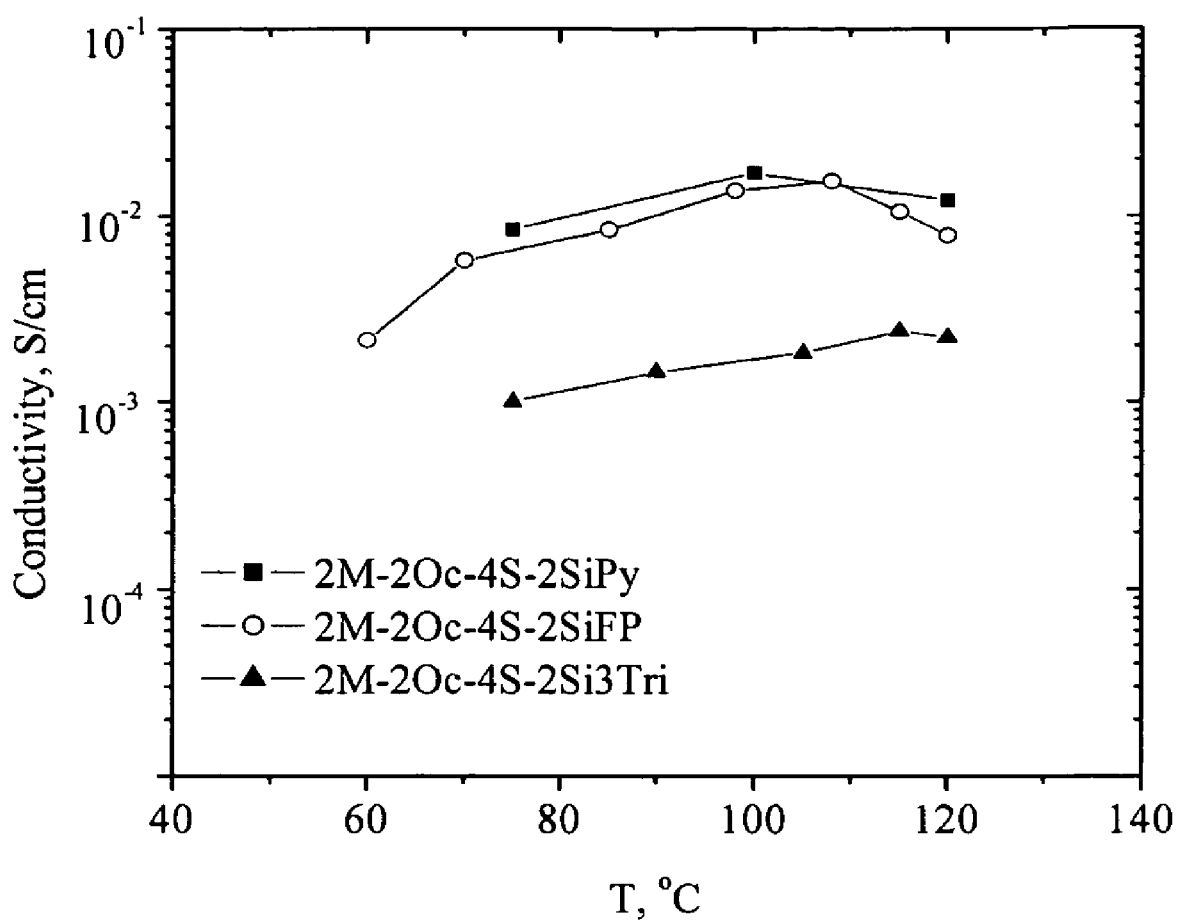
FIG. 7 shows proton conductivity of membranes grafted with acid groups (—$SO_3H$) and heterocycle rings at a relative humidity 25% at 80° C.

FIG. 7 shows proton conductivity of membranes grafted with acid groups (—$SO_3H$) and heterocycle rings with compositions of 2M-2Oc-4S-2SiHc (Hc=3Tri, Py, and FP) in a vapor of saturated $MgCl_2$ aqueous solution (relative humidity 25% at 80° C.).

EXAMPLE 37

Synthesis of Copolymers with Grafted —SO$_3$H Groups and 1H-1,2,4-triazole (Scheme 38)

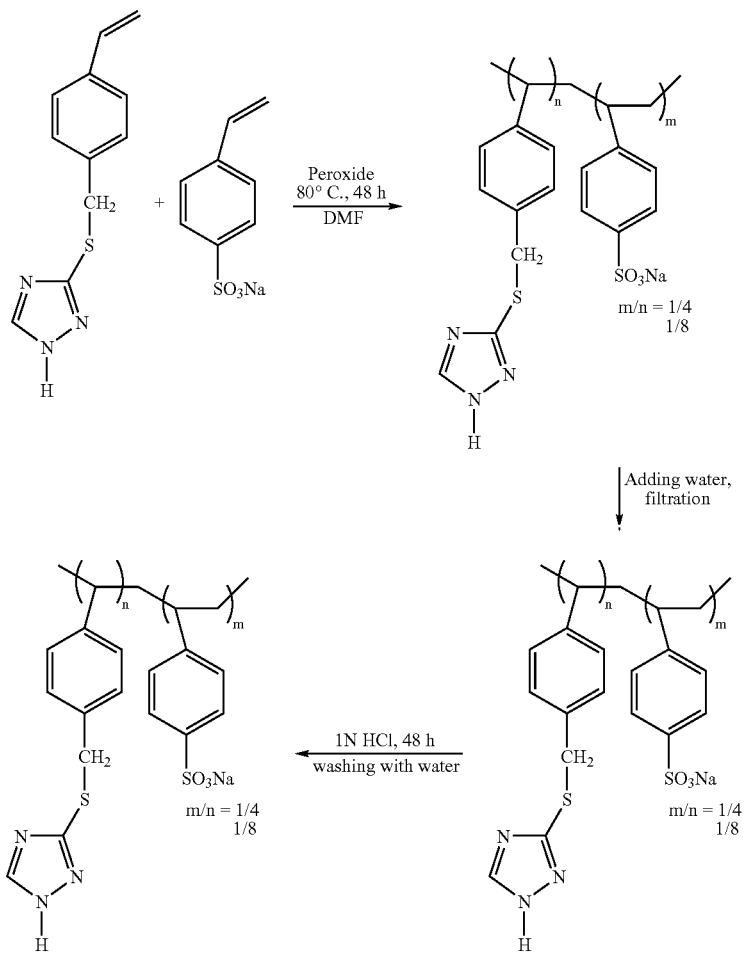

Other Examples

Example compounds according to the present invention (such as monomers and other low/medium molecular weight compounds, dimers, oligomers, polymers (including copolymers), composites, and the like) include heterocycles, such as nitrogen containing heterocycles. Heterocycles can be 5- or 6-membered single ring structures, larger ring structures, multiple ring structures, or some other ring structure, and each heterocycle may include, for example, 1, 2, 3, or more nitrogen atoms. In other examples, one or more other atoms providing a lone pair of electrons may be included in a ring structure.

New thermally stable heterocycle containing compounds can replace water in a polymer electrolyte membrane fuel cell (PEM FC) system, allowing higher operation temperature.

For example, an improved PEM comprises a polymer membrane, an acid group, and a compound including two or more nitrogen-containing heterocycles interconnected by organic chains. The acid group may be part of a free acid molecule, or be bound to the polymer membrane. The polymer membrane may include a polymer according to the present invention, a polymer according to one of our co-pending applications, or a polymer known in the art, such as Nafion™.

Examples of nitrogen-containing heterocycles include pyrazine, pyrazole, pyridazine, pyridine, pyrimidine, and pyrrole, and fused ring structures such as pyrrolizine, quinazoline, quinoline, quinolizine, quinoxaline, phenanthroline, phenazine, cinnoline, phthalazine, and the like. Other examples will be apparent to those skilled in the chemical arts.

Nitrogen-containing heterocycles may further include oxygen, sulfur, selenium, other chalcogenides, or other non-carbon elements within a ring structure. Nitrogen containing heterocycles may be halogenated, for example fluorinated. Heterocycles may be nitrogen-containing, oxygen-containing, or sulfur-containing.

Compounds according to the present invention may include heterocycles, the heterocycles including one or more non-carbon atoms such as nitrogen, oxygen, sulfur and/or other non-carbon atoms. Heterocycles may be aromatic or non-aromatic, though aromatic heterocycles are preferred. Heterocycles may be halogenated, for example, fluorinated. Other substituents are discussed below.

Heterocycles may be substituted in one or more substitutable positions, for example with a group selected from: hydroxy, amino, hydrogen, halogen (chloro-, fluoro-, iodo-, bromo-), methyl or other alkyl, aromatic, alkenyl, methoxy or other alkoxy, nitro, nitrobenzyl or other aromatic derivative, ester, sulfone, ketone, thio, thiol, amyl, allyl, allylthio, allyloxy, cyano, silyl, or other group or combination of groups. If there is more than one substituent, the substituents may be the same or different. Substituents may be chosen so as to lower pKa.

Example compounds according to the present invention include a nitrogen containing heterocycle having a pKa of equal to or less than 7 (corresponding to imidazole), for example having a pKa of equal to or less than approximately 5.2 (corresponding to pyridine), for example, a pKa equal to or less than approximately 2.4 (corresponding to 1H-1,2,4-triazole), for example, a pKa equal to or less than approximately 1.2 (corresponding to 1H-1,2,3-triazole). Tables of pKa for various heterocycles are known in the chemical art, and will not be reproduced here. The pKa used may be for the heterocycle ring structure alone, or for a molecule or analogous moiety containing the heterocycle (for example, a polymer side chain). In other examples, a heterocycle pKa is chosen so as to be equal to or less than the approximate pH of the PEM environment.

Example polymers according to the present invention may further include inorganic acid groups bound to a polymer backbone, and/or other proton solvent groups such as imidazole and derivatives thereof, such as fluorinated imidazole, for example as described in our co-pending patent applications.

Example PEMs according to the present invention may further include free acid molecules, water, insoluble inorganic acid salts, and the like to enhance proton conductivity, for example as described in our co-pending applications. Acid groups, for example as part of free acid molecules or acid groups attached to a polymer backbone, are known in the chemical arts and further discussed in our co-pending applications.

Applications of compounds described herein include ion-conducting membranes, such as proton-conducting membranes and alkali ion conducting membranes. Other PEM applications are disclosed in our co-pending applications, or will be clear to those skilled in the art. Improved fuel cells can be fabricated using PEMs at least in part including (or synthesized using) compounds disclosed herein. Other applications may include direct methanol fuel cells, electrochromic cells, capacitors and other electrochemical devices. PEMs including polymers discussed here provide high proton conductivity in a dry atmosphere and at higher temperatures; good mechanical properties; and high thermal stability.

Patents, patent applications, or publications mentioned in this specification are incorporated herein by reference to the same extent as if each individual document was specifically and individually indicated to be incorporated by reference. In particular, U.S. Prov. Pat. App. Ser. Nos. 60/539,641, 60/614,814, and 60/439,985, and our other co-pending patent applications concerning PEMs (such as Int. App. Nos. PCT/US2004/016896 and PCT/US2004/016897) are incorporated herein in their entirety.

The invention is not restricted to the illustrative examples described above. Examples are not intended as limitations on the scope of the invention. Methods, apparatus, compositions, and the like described herein are exemplary and not intended as limitations on the scope of the invention. Changes therein, other combinations, other uses, and the like will occur to those skilled in the art. The scope of the invention is defined by the scope of the claims.

Having described our invention, we claim:

1. A proton-conducting polymer including:
   a hybrid inorganic-organic matrix including silicon atoms;
   an acid group attached to the hybrid inorganic-organic matrix; and
   a nitrogen-containing heterocycle attached to the hybrid inorganic-organic matrix,
   wherein the nitrogen-containing heterocycle is selected from a group consisting of 1,2,4-triazole, 1,2,3-triazole, 1H-benzotriazole, pyrimidine, pyrazine, purine, imidazole, pyrazole, and pyridine.

2. The proton-conducting polymer of claim 1, wherein the nitrogen-containing heterocycle has at least one halogenated substituent group attached thereto.

3. The proton-conducting polymer of claim 1, wherein the nitrogen-containing heterocycle has an electron-withdrawing group attached thereto.

4. The proton-conducting polymer of claim 3, wherein the electron-withdrawing group includes at least one fluorine atom.

5. The proton-conducting polymer of claim 1, wherein the nitrogen-containing heterocycle is a fluorinated imidazole ring having a pKa of less than approximately 2.6.

* * * * *

UNITED STATES PATENT AND TRADEMARK OFFICE
CERTIFICATE OF CORRECTION

| | |
|---|---|
| PATENT NO. | : 7,576,165 B2 |
| APPLICATION NO. | : 11/044527 |
| DATED | : August 18, 2009 |
| INVENTOR(S) | : Li et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 313 days.

Signed and Sealed this

Seventh Day of September, 2010

David J. Kappos
*Director of the United States Patent and Trademark Office*